(12) United States Patent
Murakami et al.

(10) Patent No.: US 10,588,893 B2
(45) Date of Patent: Mar. 17, 2020

(54) OINTMENT CONTAINING AN OXAZOLE COMPOUND

(71) Applicant: OTSUKA PHARMACEUTICAL CO., LTD., Tokyo (JP)

(72) Inventors: Yoshihiro Murakami, Osaka (JP); Hitoshi Matsushita, Osaka (JP); Kengo Matsumoto, Osaka (JP); Minoru Okada, Osaka (JP); Yohei Yuki, Osaka (JP); Noriyuki Koyama, Osaka (JP); Naohiko Kanai, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 4 days.

(21) Appl. No.: 16/064,618

(22) PCT Filed: Dec. 27, 2016

(86) PCT No.: PCT/JP2016/008843
§ 371 (c)(1),
(2) Date: Jun. 21, 2018

(87) PCT Pub. No.: WO2017/115780
PCT Pub. Date: Jul. 6, 2017

(65) Prior Publication Data
US 2019/0000810 A1    Jan. 3, 2019

(30) Foreign Application Priority Data
Dec. 28, 2015 (JP) ................. 2015-256784

(51) Int. Cl.
*A61K 31/421* (2006.01)
*A61K 9/06* (2006.01)
*A61K 47/44* (2017.01)
*A61P 17/04* (2006.01)
*C07D 263/32* (2006.01)

(52) U.S. Cl.
CPC .............. *A61K 31/421* (2013.01); *A61K 9/06* (2013.01); *A61K 47/44* (2013.01); *A61P 17/04* (2018.01); *C07D 263/32* (2013.01)

(58) Field of Classification Search
None
See application file for complete search history.

(56) References Cited

U.S. PATENT DOCUMENTS

| 6,419,963 B1 * | 7/2002 | Niazi ................. A61K 9/0014 424/539 |
| RE46,792 E * | 4/2018 | Okada ................. C07D 263/32 |
| 2011/0212988 A1 * | 9/2011 | Masui ................. A61K 9/0014 514/291 |

FOREIGN PATENT DOCUMENTS

| WO | 2007/058338 A2 | 5/2007 |
| WO | 2014/034958 A1 | 3/2014 |

OTHER PUBLICATIONS

Pakistan Examination Report dated Nov. 13, 2017, for corresponding Pakistan Patent Application No. 826/2016.
International Search Report for PCT/JP2016/088843 dated Feb. 23, 2017 [PCT/ISA/210].
Written Opinion for PCT/JP2016/088843 dated Feb. 23, 2017 [PCT/ISA/237].

* cited by examiner

*Primary Examiner* — Sahar Javanmard
(74) *Attorney, Agent, or Firm* — Sughrue Mion, PLLC

(57) ABSTRACT

An ointment is provided. The ointment stably comprises an oxazole compound that has specific inhibitory activity against PDE4 and that is represented by the following formula (11). The ointment can be efficiently absorbed into the skin.

(11)

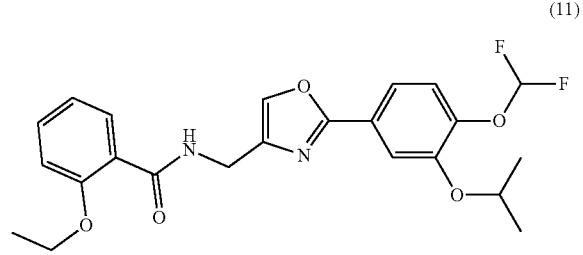

8 Claims, No Drawings

OINTMENT CONTAINING AN OXAZOLE COMPOUND

CROSS REFERENCE TO RELATED APPLICATIONS

This application is a National Stage of International Application No. PCT/JP2016/088843 filed Dec. 27, 2016, claiming priority based on Japanese Patent Application No. 2015-256784 filed Dec. 28, 2015.

TECHNICAL FIELD

The present invention relates to an ointment comprising an oxazole compound.

BACKGROUND ART

PTL 1 and 2 report an oxazole compound having specific inhibitory activity against phosphodiesterase 4 (PDE4) and a method for producing the oxazole compound. PDE4 is predominant in inflammatory cells. Inhibition of PDE4 increases intracellular cAMP levels, and increased cAMP levels down-regulate inflammatory response through expression regulation of TNF-α, IL-23, or other inflammatory cytokines. Increases in cAMP levels also increase anti-inflammatory cytokines, such as IL-10. Thus, the oxazole compound is thought to be suitable for use as an anti-inflammatory agent. For example, the oxazole compound is thought to be useful to reduce or eliminate eczema or dermatitis, including atopic dermatitis.

However, so far there has been no ointment that stably contains an oxazole compound having specific inhibitory activity against PDE4 and that can be efficiently absorbed into the skin.

CITATION LIST

Patent Literature

[PTL 1] WO2007/058338 Pamphlet (JP2009-515872A)
[PTL 2] WO2014/034958 Pamphlet (JP2015-528433A)

SUMMARY OF INVENTION

Technical Problem

An object of the present invention is to provide an ointment that stably comprises an oxazole compound having specific inhibitory activity against PDE4 and that can be efficiently absorbed into the skin.

Solution to Problem

The present inventors found that dissolving a specific oxazole compound, among oxazole compounds having specific inhibitory activity against PDE4, in a specific solvent and dissolving or dispersing the resulting solution in a base material can provide an ointment that stably contains the specific oxazole compound and that can be efficiently absorbed into the skin. The inventors further made modification and completed the present invention.

Specifically, the present invention encompasses, for example, the following subject matters.
Item 1. An ointment comprising an oxazole compound represented by the following formula (11):

[Chem. 1]

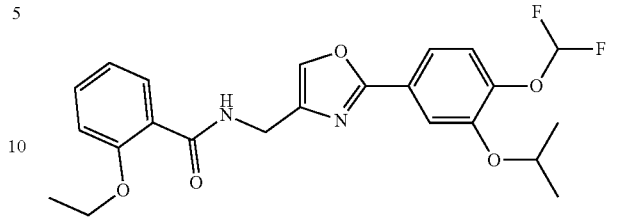

(11)

Item 2. The ointment according to Item 1, comprising the oxazole compound dissolved in a base component.
Item 3. The ointment according to Item 2, wherein the base component comprises a solvent for dissolving the oxazole compound in the solvent, and an ointment base for dispersing or dissolving the solvent in the ointment base.
Item 4. The ointment according to Item 3, wherein the ointment base comprises a hydrocarbon (preferably, at least one hydrocarbon selected from the group consisting of petrolatum, paraffin, wax, and beeswax).
Item 5. The ointment according to Item 3 or 4, wherein the solvent comprises a polar compound that is a liquid at room temperature (preferably, at least one member selected from the group consisting of ethylene carbonate, propylene carbonate, benzyl alcohol, triacetin, N-methylpyrrolidone, diethyl sebacate, diisopropyl sebacate, diethyl adipate, diisopropyl adipate, isostearyl alcohol, and isopropyl myristate).
Item 6. The ointment according to any one of Items 3 to 5, wherein the ointment base is an ointment base for dispersing the solvent in the ointment base, and the solvent in the form of droplets, in which the oxazole compound is dissolved, is dispersed in the ointment base.
Item 7. The ointment according to any one of Items 3 to 6, wherein the ointment base comprises at least beeswax.
Item 8. The ointment according to Item 7, wherein the beeswax is not chemically bleached.
Item 9. The ointment according to any one of Items 1 to 8, for use in the treatment and/or prevention of eczema and dermatitis (preferably atopic dermatitis).
Item 10. An ointment comprising:
(I) an oxazole compound represented by formula (11),
(II) a solvent comprising at least one member selected from the group consisting of ethylene carbonate, propylene carbonate, benzyl alcohol, and triacetin, and
(III) beeswax,
wherein component (II) in the form of droplets, in which component (I) is dissolved, is dispersed in component (III), and the droplets have a mean particle size of 100 μm or less.
Item A. A method for producing a compound represented by formula (3)

[Chem. 2]

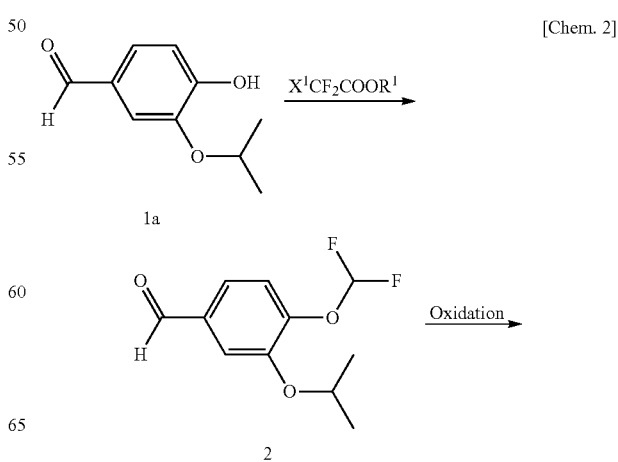

-continued

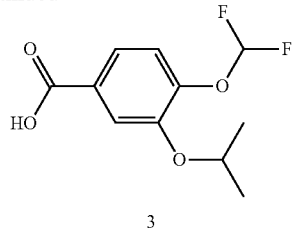

3 wherein $X^1$ represents halogen, and $R^1$ represents an alkali metal or lower alkyl, the method comprising:

(a) reacting a compound represented by formula (1a) with a compound represented by formula $X^1CF_2COOR$ to produce a compound represented by formula (2); and (b) oxidizing the compound represented by formula (2) to produce a compound represented by formula (3).

Item B. A method for producing a compound represented by formula (3)

[Chem. 3]

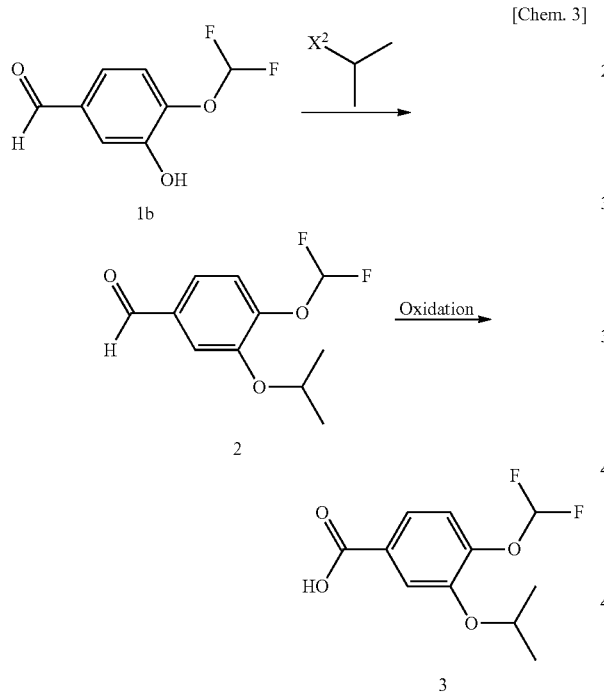

wherein $X^2$ represents halogen, the method comprising:

(a) reacting a compound represented by formula (1b) with a compound represented by formula $X^2CH(CH_3)_2$ to produce a compound represented by formula (2), and (b) oxidizing the compound represented by formula (2) to produce a compound represented by formula (3).

Advantageous Effects of Invention

The ointment according to the present invention stably contains an oxazole compound having specific inhibitory activity against PDE4, and the ointment can be efficiently absorbed into the skin.

DESCRIPTION OF EMBODIMENTS

The ointment according to the present invention comprises a specific oxazole compound, which is preferably dissolved in a base component. The oxazole compound can be contained in an ointment as an active component. The base component as used here encompasses a solvent for dissolving the oxazole compound in the solvent, and one or more other ointment bases. The ointment base is preferably an ointment base in which the solvent can be dispersed or dissolved.

In other words, the ointment according to the present invention comprises (I) a specific oxazole compound, which is preferably dissolved in a base component, and the base component includes (II) a solvent for dissolving the oxazole compound in the solvent and (III) an ointment base.

More preferably, the ointment according to the present invention is an ointment wherein component (II) in the form of droplets, in which component (I) is dissolved, is dissolved or dispersed in component (III).

Examples of oxazole compound (I) include compounds represented by the following formulae (11) and (11a) to (11s). In particular, the compound represented by formula (11) is preferable.

[Chem. 4]

(11)

TABLE 1

| Formula Number | Structural Formula |
|---|---|
| 11a | |

TABLE 1-continued

| Formula Number | Structural Formula |
|---|---|
| 11b | (structure) |
| 11c | (structure) |
| 11d | (structure) |
| 11e | (structure) |
| 11f | (structure) |
| 11g | (structure) |
| 11h | (structure) |

TABLE 1-continued

| Formula Number | Structural Formula |
| --- | --- |
| 11i | |
| 11j | |
| 11k | |
| 11l | |
| 11m | |
| 11n | |
| 11o | |

TABLE 1-continued

| Formula Number | Structural Formula |
|---|---|
| 11p | |
| 11q | |
| 11r | |
| 11s | |

These oxazole compounds can be used singly or in a combination of two or more. Specifically, the ointment of the present invention comprises at least one oxazole compound selected from the group consisting of compounds represented by formulae (11) and (11a) to (11s).

Although there is no particular limitation, oxazole compound (I) is present in the ointment in an amount of preferably 0.01 to 10 parts by weight, more preferably 0.05 to 7.5 parts by weight, still more preferably 0.1 to 5 parts by weight, per 100 parts by weight of the ointment.

As stated above, the oxazole compound is preferably dissolved in solvent (II). The solvent is preferably a polar compound that is a liquid at room temperature. Specific examples of the solvent include ethylene carbonate, propylene carbonate, benzyl alcohol, triacetin, diethyl sebacate, diisopropyl sebacate, diethyl adipate, diisopropyl adipate, isostearic acid, olive oil, hexyldodecanol, decyl oleate, isostearyl alcohol, and isopropyl myristate. Ethylene carbonate, propylene carbonate, benzyl alcohol, and triacetin are more preferable, and propylene carbonate and triacetin are still more preferable. Of these, propylene carbonate is preferable. These solvents can be used singly or in a combination of two or more. In particular, it is preferable to use ethylene carbonate or propylene carbonate alone, or a combination of ethylene carbonate or propylene carbonate with benzyl alcohol and/or triacetin.

Solvent (II) is present in the ointment in an amount of preferably more than 2 parts by weight, more preferably 2.1 parts by weight or more, and still more preferably 2.2 parts by weight or more, per part by weight of oxazole compound (I). The upper limit of the amount of solvent (II) is not particularly limited, as long as the effect of the present invention is produced. For example, the upper limit is preferably 30 parts by weight or less, more preferably 20 parts by weight or less, and still more preferably 15 parts by weight or less.

Solvent (II) is present in the ointment in an amount of preferably 0.1 to 50 parts by weight, more preferably 0.2 to 25 parts by weight, and still more preferably 0.5 to 20 parts by weight, per 100 parts by weight of the ointment.

A solution of the oxazole compound in the solvent is preferably dissolved or dispersed in the form of droplets in ointment base (III), and more preferably dispersed in the form of droplets in ointment base (III).

Known ointment bases for use in the production of ointments can be used as ointment base (III). Examples of ointment bases include hydrocarbons, and more specific examples include grease bases, particularly natural wax, petroleum wax, and other hydrocarbons. Examples of natural wax include beeswax (e.g., unbleached beeswax, non-chemically bleached beeswax, and chemically bleached beeswax), and carnauba wax. Examples of petroleum wax include paraffin and microcrystalline wax. Examples of other hydrocarbons include liquid paraffin and petrolatum (e.g., white petrolatum and yellow petrolatum). These ointment bases can be used singly or in a combination of two or more.

Ointment base (III) is present in the ointment in an amount of preferably 5 to 5000 parts by weight, more preferably 10 to 2500 parts by weight, and still more preferably 20 to 1000 parts by weight, per part by weight of oxazole compound (I).

Ointment base (III) is present in the ointment in an amount of preferably 50 to 99 parts by weight, more preferably 70 to 98 parts by weight, and still more preferably 80 to 97 parts by weight, per 100 parts by weight of the ointment.

Ointment base (III) preferably comprises at least beeswax. The beeswax for use is preferably beeswax that is not chemically bleached, including, for example, beeswax that is non-chemically bleached (non-chemically bleached beeswax) and beeswax that is not bleached (unbleached beeswax).

The beeswax is present in the ointment in an amount of preferably 0.05 to 50 parts by weight, more preferably 0.1 to 40 parts by weight, and still more preferably 0.2 to 35 parts by weight, per part by weight of oxazole compound (I).

The beeswax is present in the ointment in an amount of preferably 0.1 to 10 parts by weight, more preferably 0.2 to 9 parts by weight, still more preferably 0.4 to 8 parts by weight, even still more preferably 0.5 to 7.5 parts by weight, and particularly preferably 1 to 5 parts by weight, per 100 parts by weight of the ointment.

When other ointment bases are combined with beeswax, the combination is not particularly limited. However, for example, the combination preferably comprises at least one member selected from the group consisting of petrolatum (preferably white petrolatum), liquid paraffin, and paraffin and beeswax.

In addition to the ointment base, the ointment may comprise other additives for use in ointments (in particular, pharmaceutical additives), such as aroma components, colorants, preservatives, absorption promoters including higher alkene acids (e.g., oleic acid), or medicaments effective for treating other skin diseases.

As stated above, the ointment of the present invention is preferably an ointment wherein solvent (II), in which oxazole compound (I) is dissolved or dispersed, is dissolved or dispersed in the form of droplets in ointment base (III). Examples of the method for producing this ointment include a method comprising preparing a solution of component (I) in component (II), and mixing the solution with component (III) with stirring. Mixing with stirring can be performed with, for example, a homomixer, a paddle mixer, or a combination of these mixers.

In the use of multiple types of ointment bases (component (III)), it is preferable to mix the multiple ointment bases beforehand. In the formulation of component (III) containing multiple types of ointment bases, it is preferable to mix the ointment bases with heating to melt the solids, such as beeswax. For example, when beeswax and other ointment bases are used in combination, beeswax and other ointment bases are preferably mixed beforehand, preferably with heating.

In the case of an ointment wherein component (II), in which component (I) is dissolved, is dispersed in the form of droplets in component (III), the particle size of the droplets observed with a polarizing microscope is 100 μm or less, preferably about 40 μm or less, more preferably about 25 μm or less, and still more preferably about 20 μm or less. In particular, there exist preferably no droplets having a particle size of more than 100 μm, more preferably no droplets having a particle size of more than 40 μm, still more preferably no droplets having a particle size of more than 25 μm, and even still more preferably no droplets having a particle size of more than 20 μm. A desired mean particle size of the droplets is achieved by adjusting the stirring rate at which the solution is mixed with component (III) with stirring.

The oxazole compound represented by formula (11) is a known compound disclosed in PTL 1 and 2, and can be produced in accordance with the procedure described in PTL 1 or 2.

The oxazole compound represented by formula (11) can also be produced as described below. The compounds used as starting materials below are known or easily produced from known compounds.

Specifically, compound (3) is first synthesized, and then compound (7) is synthesized from compound (3). Subsequently, compound (11) is synthesized from compound (7). In this specification, a compound represented by formula A may be indicated as compound A or compound (A).

[Chem. 5]

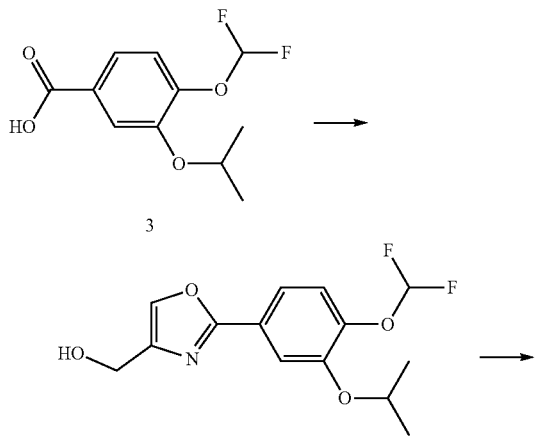

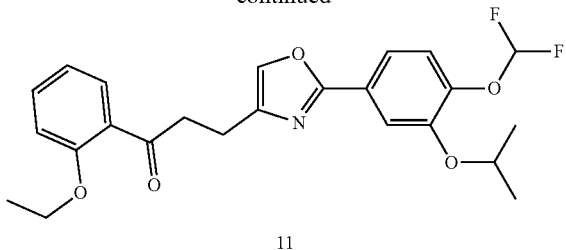

11

Production of Compound (3)

Compound (3) can be produced, for example, through the reaction steps illustrated in the following reaction scheme.

[Chem. 6]

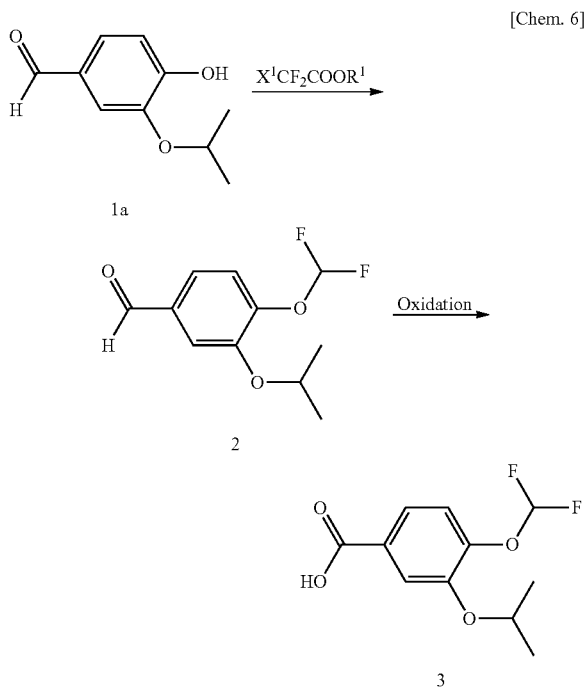

Compound (1a)+Compound $X^1CF_2COOR$→Compound (2)

Compound (2) can be produced by reacting compound (1a) with compound $X^1CF_2COOR^1$ in the presence of a base.

In compound $X^1CF_2COOR^1$, $X^1$ represents halogen, and the halogen includes fluorine, chlorine, bromine, and iodine, with chlorine, bromine, and iodine being preferable, and chlorine being more preferable.

$R^1$ represents an alkali metal or lower alkyl. The alkali metal includes lithium, sodium, and potassium, with sodium being preferable. The lower alkyl includes C1-C6 (in particular, C1-C4) linear or branched alkyl. Specific examples include methyl, ethyl, n-propyl, isopropyl, n-butyl, isobutyl, sec-butyl, tert-butyl, 1-ethyl propyl, n-pentyl, neopentyl, n-hexyl, isohexyl, and 3-methyl pentyl, with methyl and ethyl being preferable.

The reaction can be performed in the presence of a common solvent. The solvent can be any solvent that does not adversely affect the reaction. Examples of the solvent include ketone solvents (e.g., acetone and methyl ethyl ketone), ether solvents (e.g., tetrahydrofuran, dioxane, diethyl ether, and diglyme), ester solvents (e.g., methyl acetate and ethyl acetate), aprotic polar solvents (e.g., acetonitrile, N,N-dimethylformamide, and dimethyl sulfoxide), halogenated hydrocarbon solvents (e.g., methylene chloride and ethylene chloride), and combinations of these solvents. The solvent is preferably N,N-dimethylformamide.

The base for use can be known inorganic bases or organic bases. Examples of inorganic bases include alkali metals (e.g., sodium and potassium), alkali metal hydrogen carbonates (e.g., lithium hydrogen carbonate, sodium hydrogen carbonate, and potassium hydrogen carbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), alkali metal lower (C1-C3) alkoxides (e.g., sodium methoxide and sodium ethoxide), and alkali metal hydrides (e.g., sodium hydride and potassium hydride). Examples of organic bases include trialkyl amines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are a liquid, these bases can also be used as a solvent. These bases are used singly or in a combination of two or more. The base is preferably an alkali metal carbonate (in particular, sodium carbonate or potassium carbonate).

The amount of the base for use is typically 1 to 10 moles, and preferably 1 to 6 moles, per mole of compound (1a).

The reaction can be performed by optionally adding an alkali metal iodide, such as potassium iodide or sodium iodide, as a reaction accelerator to the reaction system.

When a reaction accelerator is used, the amount of the reaction accelerator is typically at least 0.01 moles, and preferably about 0.1 to 2 moles, per mole of $X^1CF_2COOR^1$.

The proportion of compound (1a) and compound $X^1CF_2COOR$ is typically at least 1 mole, preferably about 1 to 5 moles of compound $X^1CF_2COOR^1$, per mole of compound (1a).

The reaction temperature is not particularly limited, and the reaction can be typically performed under any of the following conditions: with cooling, at room temperature, or with heating. The reaction is preferably performed at a temperature of about 80 to 120° C. for 1 to 30 hours.

Compound (2)→Compound (3)

Compound (3) can be produced by oxidizing compound (2). Specifically, for example, compound (3) is produced by subjecting compound (2) to reaction in a solvent in the presence of an oxidant.

When compound (2) is reacted in a solvent in the presence of an oxidant, examples of the solvent for use include water; alcohols, such as methanol, ethanol, propanol, isopropyl alcohol, n-butanol, tert-butanol, and ethylene glycol; halogenated hydrocarbons, such as dichloromethane, chloroform, and carbon tetrachloride; ethers, such as diethyl ether, tetrahydrofuran, dioxane, monoglyme, and diglyme; ketones, such as acetone and methyl ethyl ketone; aromatic hydrocarbons, such as benzene, o-dichlorobenzene, toluene, and xylene; esters, such as methyl acetate, ethyl acetate, and butyl acetate; aprotic polar solvents, such as acetonitrile, N,N-dimethylformamide, and hexamethylphosphoric triamide; and combinations of these solvents.

Oxidants include halous acids, such as chlorous acid, iodous acid, and bromous acid; alkali metal salts of halous acids, such as sodium chlorite, sodium iodite, sodium bromite, potassium chlorite, potassium iodite, and potassium bromite; alkali metal salts of permanganic acid, such as potassium permanganate; chromic acid or alkali metal salts thereof, such as chromium oxide (VI), sodium dichromate, and potassium dichromate; and nitric acid. When using an alkali metal salt of permanganic acid, it is preferable to perform reaction in the presence of an inorganic base, such as potassium hydroxide, sodium hydroxide, sodium carbonate, or potassium carbonate. When using chromic acid or an alkali metal salt thereof, it is preferable to perform reaction in the presence of a mineral acid such as sulfuric acid, or an organic acid such as acetic acid. Of these, in particular, halous acids, and alkali metal salts of halous acids are particularly preferable.

The amount of the oxidant for use is typically 0.5 to 1 mole or more, and preferably 1 to 10 moles, per mole of compound (2).

The reaction temperature is typically about −20 to 50° C., and preferably about −20° C. to room temperature (25° C.). The reaction time is about 1 to 30 hours.

Compound (3) can be produced through the reaction steps illustrated in the following reaction scheme.

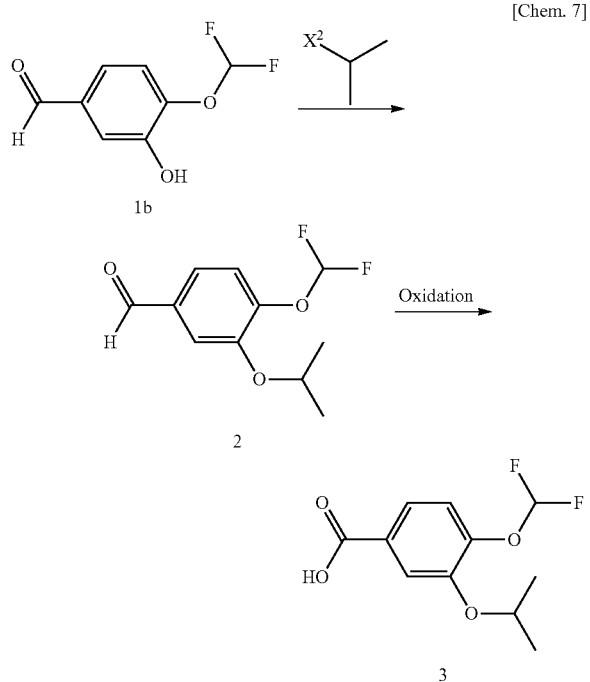

[Chem. 7]

Compound (1b)+Compound $X^2CH(CH_3)_2$→Compound (2)

Compound (2) can also be produced by reacting compound (1a) with compound $X^2CH(CH_3)_2$ in the presence of a base.

In compound $X^2CH(CH_3)_2$, $X^2$ represents halogen, and the halogen includes fluorine, chlorine, bromine, and iodine, with chlorine, bromine, and iodine being preferable, and bromine being more preferable.

The reaction can be performed in the presence of a common solvent. The solvent can be any solvent that does not adversely effect the reaction. Examples of the solvent include ketone solvents (e.g., acetone and methyl ethyl ketone), ether solvents (e.g., tetrahydrofuran, dioxane, diethyl ether, and diglyme), ester solvents (e.g., methyl acetate and ethyl acetate), aprotic polar solvents (e.g., acetonitrile, N,N-dimethylformamide, and dimethyl sulfoxide), halogenated hydrocarbon solvents (e.g., methylene chloride and ethylene chloride), and combinations of these solvents. The solvent is preferably N,N-dimethylformamide.

The base for use can be known inorganic bases or organic bases. Examples of inorganic bases include alkali metals (e.g., sodium and potassium), alkali metal hydrogen carbonates (e.g., lithium hydrogen carbonate, sodium hydrogen carbonate, and potassium hydrogen carbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), alkali metal lower (C1-C3) alkoxides (e.g., sodium methoxide and sodium ethoxide), and alkali metal hydrides (e.g., sodium hydride and potassium hydride). Organic bases include trialkyl amines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are a liquid, these bases can also be used as a solvent. These bases are used singly or in a combination of two or more. The base is preferably an alkali metal carbonate (in particular, sodium carbonate or potassium carbonate).

The amount of the base for use is typically 1 to 10 moles, and preferably 1 to 6 moles, per mole of compound (1b).

The reaction can be performed by optionally adding an alkali metal iodide, such as potassium iodide or sodium iodide, as a reaction accelerator to the reaction system.

When a reaction accelerator is used, the amount of the reaction accelerator is typically at least 0.01 moles, and preferably about 0.1 to 2 moles, per mole of $X^2CH(CH_3)_2$.

The proportion of compound (1b) and compound $X^2CH(CH_3)_2$ for use may be typically at least 1 mole, and preferably about 1 to 5 moles of compound $X^2CH(CH_3)_2$, per mole of compound (1b).

The reaction temperature is not particularly limited, and the reaction can be typically performed under any of the following conditions: with cooling, at room temperature, or with heating. The reaction is preferably performed at a temperature within the range of around room temperature to about 85° C. for 1 to 30 hours.

The method for producing compound (3) from compound (2) is as described above.

Production of Compound (7)

Compound (7) can be produced, for example, through the reaction steps illustrated in the following reaction scheme.

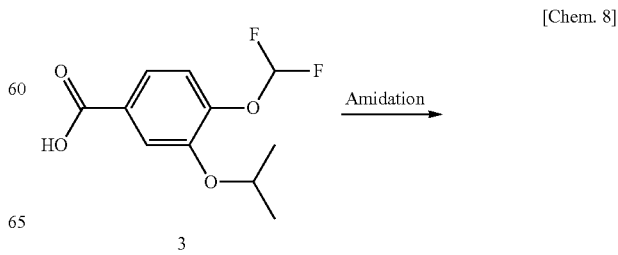

[Chem. 8]

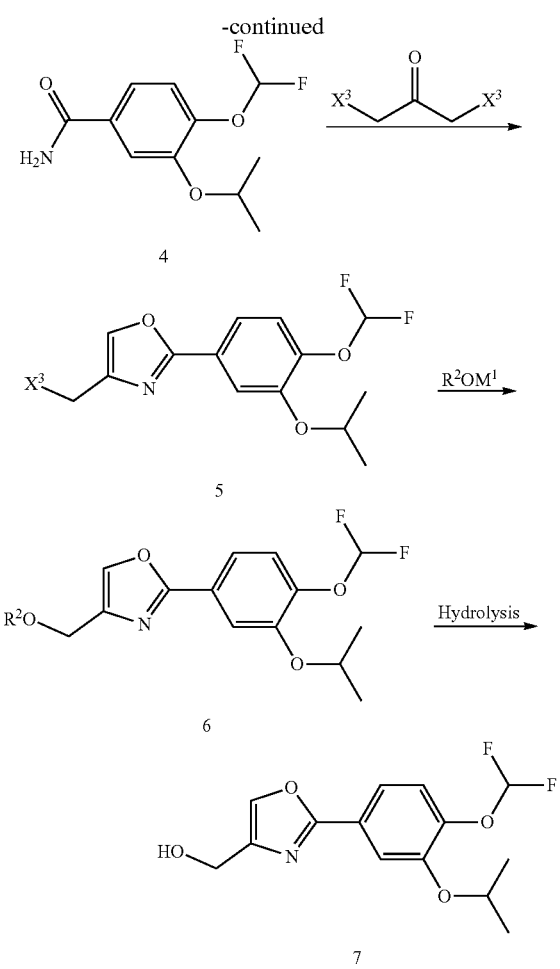

Compound (3)→Compound (4)

Compound (4) can be produced by subjecting compound (3) to condensation reaction with ammonia (amidation reaction). The reaction can be typically performed by reacting compound (3) with ammonia in a solvent in the presence of a condensation agent.

The solvent can be any solvent that does not adversely effect the reaction. Examples of the solvent include halogenated aliphatic hydrocarbon solvents (e.g., methylene chloride, chloroform, and ethylene chloride), ketone solvents (e.g., acetone and methyl ethyl ketone), ether solvents (e.g., tetrahydrofuran, dioxane, diethyl ether, dimethoxyethane, and diglyme), aromatic hydrocarbons (e.g., toluene and xylene), aprotic polar solvents (e.g., acetonitrile, N,N-dimethylformamide, N-methylpyrrolidone, and dimethyl sulfoxide), and combinations of these solvents. The solvent is preferably acetonitrile.

Examples of the condensation agent include 1,1'-carbonyl diimidazole (CDI), dicyclohexyl carbodiimide (DCC), diisopropyl carbodiimide (DIC), 1-ethyl-3-(3-dimethylaminopropyl)carbodiimide hydrochloride (EDC or WSC), diphenylphosphoryl azide (DPPA), benzotriazol-1-yloxy-tris(dimethylamino)phosphonium salts (e.g., benzotriazol-1-yloxy-tris(dimethylamino)phosphonium hexafluorophosphate), and 2-chloro-4,6-dimethoxytriazine (CDMT). The condensation agent is preferably CDI.

The amount of the condensation agent for use is typically at least 1 mole, and preferably about 1 to 5 moles, per mole of compound (3).

Together with the condensation agent, an additive (activator), such as 1-hydroxy benzotriazole (HOBt) and N-hydroxy succinimide (HOSu), may optionally be used.

When the additive is used, the amount of the additive is typically at least 1 mole, and preferably about 1 to 5 moles, per mole of the condensation agent.

The reaction can also be performed by optionally adding a base. Examples of the base include tertiary amines, such as triethylamine and N,N-diisopropylethylamine; and nitrogen-containing aromatic compounds, such as pyridine and 4-dimethylaminopyridine.

When a base is used, the amount of the base is typically at least 1 mole, and preferably about 1 to 5 moles, per mole of compound (5).

Ammonia is typically used as ammonia water. The amount of ammonia for use is typically at least 1 mole, and preferably about 1 to 10 moles, per mole of compound (3).

The reaction is typically performed by reacting compound (3) with a condensation agent, optionally with an additive, to prepare an activated ester, and reacting the activated ester with ammonia.

The reaction temperature for the preparation of the activated ester and subsequent reaction with ammonia is not particularly limited. The preparation and the reaction can be typically performed under any of the following conditions: with cooling, at room temperature, or with heating. The reaction is preferably performed at a temperature within the range of ice cooling temperature to about room temperature for 1 to 30 hours.

Compound (4)→Compound (5)

Compound (5) can be produced by reacting compound (4) with compound $CO(CH_2X^3)_2$.

In compound $CO(CH_2X^3)_2$, $X^3$ represents halogen. The halogen represented by $X^3$ includes fluorine, chlorine, bromine, and iodine, with chlorine, bromine, and iodine being preferable.

The reaction can be performed in the presence of a common solvent. The solvent can be any solvent that does not adversely effect the reaction. Examples of the solvent include halogenated aliphatic hydrocarbon solvents (e.g., methylene chloride, chloroform, and ethylene chloride), ketone solvents (e.g., acetone and methyl ethyl ketone), ether solvents (e.g., tetrahydrofuran, dioxane, diethyl ether, dimethoxyethane, and diglyme), aromatic hydrocarbons (e.g., toluene and xylene), aprotic polar solvents (e.g., acetonitrile, N,N-dimethylformamide, N-methylpyrrolidone, and dimethyl sulfoxide), and combinations of these solvents. The solvent is preferably an aromatic hydrocarbon (e.g., toluene and xylene).

The proportion of compound (4) and compound $CO(CH_2X^3)_2$ for use is typically at least 1 mole, preferably about 1 to 5 moles of compound $CO(CH_2X^3)_2$, per mole of compound (4).

Optionally, a dehydrating agent may be used. Examples of the dehydrating agent include synthetic zeolite, which specifically includes molecular sieves (MS)3A, MS4A, and other similar zeolite with fine pores.

The reaction temperature is not particularly limited, and the reaction can be typically performed under any of the following conditions: with cooling, at room temperature, or with heating. The reaction is preferably performed at a temperature within the range of around room temperature to about 200° C. for 1 to 30 hours. The use of this method enables the oxazole ring to form at a high yield.

Compound (5)→Compound (6)

Compound (6) can be produced by reacting compound (5) with compound R²OM¹. In compound R²OM¹, R² represents alkanoyl, and M¹ represents an alkali metal.

The alkanoyl represented by R² includes C1-C6 (in particular, C1-C4) linear or branched alkanoyl. Specific examples of the alkanoyl include formyl, acetyl, n-propionyl, isopropionyl, n-butyryl, isobutyryl, sec-butyryl, tert-butyryl, and hexanoyl, with formyl, acetyl, n-propionyl, and isopropionyl being preferable, and acetyl being more preferable.

The alkali metal represented by M¹ includes lithium, sodium, and potassium, with sodium and potassium being preferable.

Specific examples of compound R²CM include sodium acetate and potassium acetate.

The reaction can be performed in the presence of a common solvent. The solvent can be any solvent that does not adversely affect the reaction. Examples of the solvent include ketone solvents (e.g., acetone and methyl ethyl ketone), ether solvents (e.g., tetrahydrofuran, dioxane, diethyl ether, and diglyme), ester solvents (e.g., methyl acetate and ethyl acetate), aprotic polar solvents (e.g., acetonitrile, N,N-dimethylformamide, and dimethyl sulfoxide), halogenated hydrocarbon solvents (e.g., methylene chloride and ethylene chloride), and combinations of these solvents. The solvent is preferably N,N-dimethylformamide.

The proportion of compound (5) and compound R²OM¹ for use is typically at least 1 mole, and preferably about 1 to 5 moles of compound R²COM, per mole of compound (5).

The reaction temperature is not particularly limited, and the reaction can be typically performed under any of the following conditions: with cooling, at room temperature, or with heating. The reaction may be preferably performed at a temperature within the range of around room temperature to about 120° C. for 1 to 30 hours.

Compound (6)→Compound (7)

Compound (7) can be produced by hydrolyzing compound (6). The hydrolysis of compound (6) can be typically performed in a solvent in the presence of a base.

The solvent can be any solvent that does not adversely affect the reaction. Examples of the solvent include water, alcohol solvents (e.g., methanol, ethanol, isopropanol, and n-butanol), ketone solvents (e.g., acetone and methyl ethyl ketone), ether solvents (e.g., tetrahydrofuran, dioxane, diethyl ether, dimethoxyethane, and diglyme), and acetonitrile. Preferable examples of the solvent include a combination solvent of water and an alcohol solvent (methanol or ethanol). Alcohol solvents (in particular, methanol and ethanol) are preferable.

Examples of the base include alkali metal hydroxides (e.g., lithium hydroxide, sodium hydroxide, potassium hydroxide, and cesium hydroxide). Typically, alkali metal hydroxides can be used in the form of an aqueous solution. Examples of the aqueous solution include sodium hydroxide aqueous solution.

The amount of the base for use is typically at least 1 mole, and preferably about 1 to 5 moles, per mole of compound (6).

The reaction temperature is not particularly limited, and the reaction can be typically performed under any of the following conditions: with cooling, at room temperature, or with heating. The reaction is preferably performed at a temperature within the range of around room temperature to about 85° C. for 1 to 30 hours.

Production of Compound (11)

Compound (11) can be produced, for example, through the reaction steps illustrated in the following reaction scheme.

[Chem. 9]

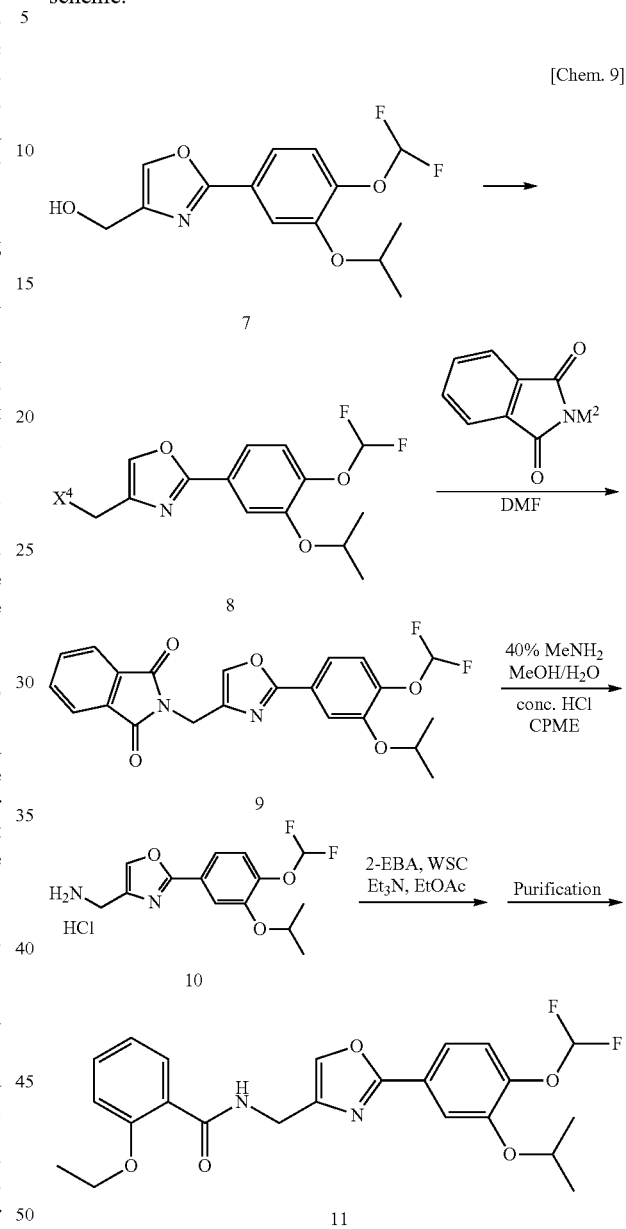

Compound (7)→Compound (8)

Compound (8) can be produced by converting the hydroxy group of compound (7) into leaving group (X⁴).

Examples of the leaving group represented by X⁴ include halogen (e.g., fluorine, chlorine, bromine, and iodine) and organic sulfonyloxy (e.g., p-toluenesulfonyloxy, methanesulfonyloxy, trifluoromethanesulfonyloxy, nonafluorobutanesulfonyloxy, and o-nitrobenzolsulfonyloxy). Halogen is preferable, and bromine is more preferable.

Compound (8'), wherein the leaving group represented by X⁴ is an organic sulfonyloxy, can be produced by reacting compound (7) with an organic sulfonyl halide or organic sulfonic acid anhydride containing the organic sulfonyl group in a solvent in the presence of a base.

The solvent can be any solvent that does not adversely affect the reaction. Examples of the solvent include ketone solvents (e.g., acetone and methyl ethyl ketone), ether solvents (e.g., tetrahydrofuran, dioxane, diethyl ether, dimethoxyethane, and diglyme), ester solvents (e.g., methyl acetate and ethyl acetate), aprotic polar solvents (e.g., acetonitrile, N,N-dimethylformamide, and dimethyl sulfoxide), halogenated hydrocarbon solvents (e.g., methylene chloride and ethylene chloride), and combinations of these solvents. The solvent is preferably ester solvents (in particular, ethyl acetate etc.).

The base for use can be known inorganic bases or organic bases. Examples of the inorganic bases include alkali metal hydrogen carbonates (e.g., lithium hydrogen carbonate, sodium hydrogen carbonate, and potassium hydrogen carbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), and alkali metal hydrides (e.g., sodium hydride and potassium hydride). The organic bases include trialkyl amines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are a liquid, these bases can also be used as a solvent. These bases can be used singly or in a combination of two or more. The base is preferably N,N-diisopropylethylamine, and triethylamine, and more preferably N,N-diisopropylethylamine. In particular, N,N-diisopropylethylamine is preferable because the use of N,N-diisopropylethylamine can significantly increase the yield.

Examples of the organic sulfonyl halide include p-toluenesulfonyl halide, methanesulfonyl halide, trifluoromethanesulfonyl halide, nonafluorobutanesulfonyl halide, and o-nitrobenzolsulfonyl halide. Examples of the halide include chloride and bromide, with chloride being preferable. Particularly preferable organic sulfonyl halide includes methanesulfonyl chloride.

Examples of the organic sulfonic acid anhydride include p-toluenesulfonic acid anhydride, methanesulfonic acid anhydride, trifluorosulfonic acid anhydride, nonafluorobutanesulfonic acid anhydride, and o-nitrobenzenesulfonic acid anhydride.

The amount of the base for use is typically 1 to 10 moles, and preferably 1 to 6 moles, per mole of compound (7).

The amount of the organic sulfonyl halide or organic sulfonic acid anhydride for use is typically 1 to 5 moles, and preferably 1 to 2 moles, per mole of compound (7).

The reaction temperature is not particularly limited, and the reaction can be typically performed under any of the following conditions: with cooling, at room temperature, or with heating. The reaction is preferably performed at a temperature of about 0 to 60° C. for 1 to 30 hours.

The reaction described above produces compound (8'), wherein the leaving group represented by $X^4$ is an organic sulfonyloxy.

Compound (8"), wherein the leaving group represented by $X^4$ is halogen, can be produced by reacting compound (8') with a halogenating agent in a solvent. When the leaving group represented by $X^4$ is halogen, the halogen includes fluorine, chlorine, bromine, and iodine, with chlorine, bromine, and iodine being preferable and chlorine being more preferable.

The solvent can be any solvent that does not adversely affect the reaction. Examples of the solvent include ketone solvents (e.g., acetone and methyl ethyl ketone), ether solvents (e.g., tetrahydrofuran, dioxane, diethyl ether, dimethoxyethane, and diglyme), ester solvents (e.g., methyl acetate and ethyl acetate), aprotic polar solvents (e.g., acetonitrile, N,N-dimethylformamide, and dimethyl sulfoxide), halogenated hydrocarbon solvents (e.g., methylene chloride and ethylene chloride), and combinations of these solvents.

Examples of the halogenating agent include alkali metal halides (e.g., lithium chloride, lithium bromide, and lithium iodide), and quaternary ammonium halides (e.g., tetrabutylammonium chloride and tetrabutylammonium bromide). The halogenating agent is preferably an alkali metal halide (in particular, lithium bromide).

The amount of the halogenating agent for use is typically 1 to 5 moles, and preferably 1 to 3 moles, per mole of compound (8').

The reaction temperature is not particularly limited, and the reaction can be typically performed under any of the following conditions: with cooling, at room temperature, or with heating. The reaction is preferably performed at a temperature about 0 to 60° C. for 1 to 30 hours.

The step of producing compound (8') from compound (7) and the step of producing compound (8") from compound (8') are each independently performed. Alternatively, both steps can be performed in one pot.

The obtained compound (8) (including compounds (8') and (8")) is subjected to the following reaction step.
Compound (8)→Compound (9)

Compound (9) can be produced by reacting compound (8) with a compound represented by the following formula:

[Chem. 10]

wherein $M^2$ represents an alkali metal (which may be hereinafter referred to as "phthalimide $M^2$ compound"). Examples of the alkali metal represented by $M^2$ include lithium, sodium, and potassium, with potassium being preferable.

The reaction can be performed in a common solvent. The solvent can be any solvent that does not adversely affect the reaction. Examples of the solvent include ketone solvents (e.g., acetone and methyl ethyl ketone), ether solvents (e.g., tetrahydrofuran, dioxane, diethyl ether, dimethoxyethane, and diglyme), ester solvents (e.g., methyl acetate and ethyl acetate), aprotic polar solvents (e.g., acetonitrile, N,N-dimethylformamide, and dimethyl sulfoxide), halogenated hydrocarbon solvents (e.g., methylene chloride and ethylene chloride), and combinations of these solvents. The solvent is more preferably N,N-dimethylformamide.

The proportion of compound (8) and phthalimide $M^2$ compound is typically at least 1 mole, and preferably about 1 to 5 moles of phthalimide $M^2$ compound, per mole of compound (8).

The reaction temperature is not particularly limited, and the reaction can be typically performed under any of the following conditions: with cooling, at room temperature, or with heating. The reaction is performed at a temperature of about 0 to 100° C. for 1 to 30 hours.

Compound (9)→Compound (10)

Compound (10) can be produced by reacting compound (9) with methylamine.

The reaction can be performed in a common solvent. The solvent can be any solvent that does not adversely affect the reaction. Examples of the solvent include water, alcohol solvents (e.g., methanol, ethanol, isopropanol, n-butanol, trifluoroethanol, and ethylene glycol), ether solvents (e.g., tetrahydrofuran, dioxane, diethyl ether, dimethoxyethane, and diglyme), aprotic polar solvents (e.g., acetonitrile, N,N-dimethylformamide, and dimethyl sulfoxide), and combinations of these solvents. The solvent is preferably a combination solvent of water and an alcohol solvent (in particular, methanol or ethanol).

Methylamine can be typically used in the form of a methylamine aqueous solution.

The amount of methylamine for use is typically 1 to 10 moles, and preferably 1 to 5 moles, per mole of compound (9).

The reaction temperature is not particularly limited, and the reaction can be typically performed under any of the following conditions: with cooling, at room temperature, or with heating. The reaction is preferably performed at a temperature within the range of around room temperature to about 100° C. for 10 minutes to 30 hours.

Obtained compound (10) is a primary amine compound. Compound (10) can optionally be converted into a salt formed with an acid from the standpoint of handleability. The salt can be formed in accordance with a known method. The acid can be selected from a wide range of organic acids or inorganic acids. The organic acids include organic carboxylic acids, such as formic acid, acetic acid, lactic acid, tartaric acid, and succinic acid; and sulfonic acids, such as methanesulfonic acid, toluenesulfonic acid, and naphthalenesulfonic acid. Examples of the inorganic acids include hydrochloric acid, sulfuric acid, nitric acid, and phosphoric acid.

The solvent for use in forming the salt can be any solvent that does not adversely affect the reaction. Examples of the solvent include alcohol solvents (e.g., methanol, ethanol, isopropanol, n-butanol, trifluoroethanol, and ethylene glycol), ketone solvents (e.g., acetone and methyl ethyl ketone), ether solvents (e.g., cyclopentyl methyl ether (CPME), tetrahydrofuran, dioxane, diethyl ether, dimethoxyethane, and diglyme), ester solvents (e.g., methyl acetate and ethyl acetate), aprotic polar solvents (e.g., acetonitrile, N,N-dimethylformamide, and dimethyl sulfoxide), and combinations of these solvents. The solvent is preferably ether solvents (in particular, CPME).

Compound (10)→Compound (11)

Compound (11) can be produced by subjecting compound (10) to condensation reaction with 2-ethoxybenzoic acid.

The condensation reaction is typically performed in a solvent in the presence of a condensation agent. When compound (10) is a salt formed with an acid, compound (10) may be converted into a free primary amine by removing the acid from the salt using a base (e.g., inorganic bases, such as sodium hydroxide, potassium hydroxide, sodium carbonate, and sodium hydrogen carbonate; and organic bases, such as triethylamine and N,N-diisopropylethylamine) before performing the reaction.

The solvent can be any solvent that does not adversely affect the reaction. Examples of the solvent include halogenated aliphatic hydrocarbon solvents (e.g., methylene chloride, chloroform, and ethylene chloride), ketone solvents (e.g., acetone and methyl ethyl ketone), ether solvents (e.g., tetrahydrofuran, dioxane, diethyl ether, dimethoxyethane, and diglyme), ester solvents (e.g., methyl acetate and ethyl acetate), aromatic hydrocarbons (e.g., toluene and xylene), aprotic polar solvents (e.g., acetonitrile, N,N-dimethylformamide, N-methylpyrrolidone, and dimethyl sulfoxide), and combinations of these solvents. The solvent is preferably ketone solvents (in particular, acetone and methyl ethyl ketone), ether solvents (in particular, tetrahydrofuran, dioxane, diethyl ether, and dimethoxyethane), and ester solvents (e.g., methyl acetate and ethyl acetate).

Examples of the condensation agent include 1,1'-carbonyl diimidazole (CDI), dicyclohexyl carbodiimide (DCC), diisopropyl carbodiimide (DIC), 1-ethyl-3-(3-dimethylaminopropyl) carbodiimide hydrochloride (EDC or WSC), diphenylphosphoryl azide (DPPA), benzotriazol-1-yloxy-tris(dimethylamino)phosphonium salts (e.g., benzotriazol-1-yloxy-tris(dimethylamino)phosphonium hexafluorophosphate), and 2-chloro-4,6-dimethoxytriazine (CDMT). The condensation agent is preferably CDI or WSC.

The amount of the condensation agent for use is typically at least 0.5 moles, and preferably about 1 to 5 moles, per mole of 2-ethoxybenzoic acid.

Together with the condensation agent, an additive (activator), such as 1-hydroxy benzotriazole (HOBt) or N-hydroxy succinimide (HOSu), can optionally be used.

The amount of the additive for use is typically at least 1 mole, and preferably about 1 to 5 moles, per mole of the condensation agent.

The reaction can be performed by optionally adding a base. Examples of the base include tertiary amines, such as triethylamine and N,N-diisopropylethylamine; and nitrogen-containing aromatic compounds, such as pyridine and 4-dimethylaminopyridine.

When a base is used, the amount of the base may be typically at least 0.5 moles, and preferably about 1 to 5 moles, per mole of the condensation agent.

The proportion of compound (10) and 2-ethoxybenzoic acid is typically at least 1 mole, and preferably about 1 to 2 moles of 2-ethoxybenzoic acid, per mole of compound (10).

The reaction temperature is not particularly limited, and the reaction can be typically performed under any of the following conditions: with cooling, at room temperature, or with heating. The reaction is preferably performed at a temperature of about 0 to 100° C. for 1 to 30 hours.

In this specification, the term "comprising" includes "consisting essentially of" and "consisting of." The present invention covers all combinations of the elements described in this specification.

EXAMPLES

The following describes the present invention in detail. However, the present invention is not limited to the Examples.

Production Example 1: Production 1 of Compound (3)

Compound (3) was produced in accordance with the following reaction scheme.

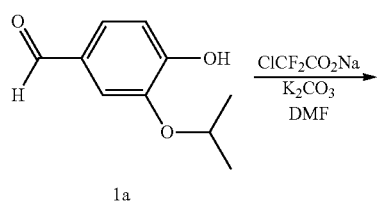

[Chem. 11]

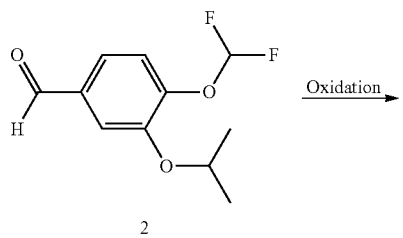

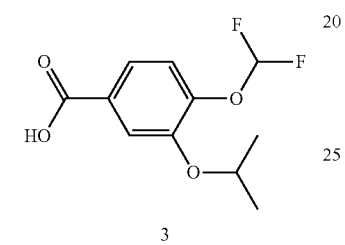

10.00 g (55.5 mmol) of compound (1a) and 9.20 g (66.6 mmol) of potassium carbonate were added to 40 ml of N,N-dimethylformamide and 6 ml of water, and the mixture was stirred until exotherm subsided. 16.92 g (111 mmol) of sodium chlorodifluoroacetate was added thereto, and the mixture was reacted at 95 to 110° C. for 3 hours. 80 ml of butyl acetate and 80 ml of water were added to the reaction solution, and the solution was partitioned. 80 ml of water was added again to the organic layer, followed by partitioning. 3 ml of concentrated hydrochloric acid was added to the organic layer, and the mixture was stirred at 60 to 70° C. for 30 minutes. 40 ml of water and 10 ml of a 25% sodium hydroxide aqueous solution were added to the reaction solution, and the mixture was partitioned. 5.93 g (61.1 mmol) of sulfamic acid and 10 ml of water were added to the organic layer, and 22.08 g (61.0 mmol) of a 25% sodium chlorite aqueous solution was added dropwise thereto at a temperature of 20° C. or below. The mixture was reacted at 20° C. or below for 15 minutes, and 10 ml of a 25% sodium hydroxide aqueous solution was added dropwise thereto at a temperature of 20° C. or below, followed by pouring in 83.95 g (66.6 mmol) of a 10% sodium sulfite aqueous solution. Additionally, 2 ml of concentrated hydrochloric acid was added and the mixture was partitioned, followed by concentration of the organic layer under reduced pressure. 40 ml of methanol, 80 ml of water, and 10 ml of a 25% sodium hydroxide aqueous solution were added to the concentrated residue to dissolve the residue, and 5 ml of concentrated hydrochloric acid was added dropwise thereto to precipitate crystals. The precipitated crystals were collected by filtration and dried at 80° C., thereby obtaining 11.81 g (yield: 86.4%) of compound (3) as a white powder.

$^1$H-NMR (CDCl$_3$) δ: 7.70 (2H, dd, J=6.4 Hz, 2.0 Hz), 7.22 (1H, d, J=9.2 Hz), 6.66 (1H, t, J=74.8 Hz), 4.66 (1H, sept, J=6.0 Hz), 1.39 (6H, d, J=6.0 Hz).

Production Example 2: Production 2 of Compound (3)

Compound (3) was produced in accordance with the following reaction scheme.

[Chem. 12]

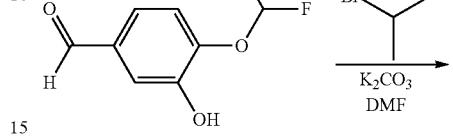

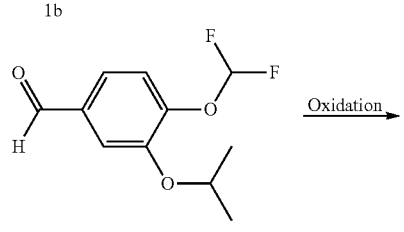

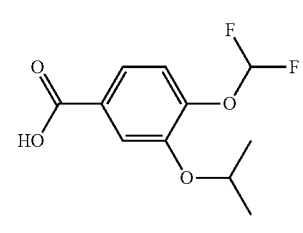

10.00 g (53.2 mmol) of compound (1b), 9.55 g (69.1 mmol) of potassium carbonate, and 8.50 g (69.1 mmol) of isopropyl bromide were added to 40 ml of N,N-dimethylformamide, and the mixture was reacted at 75 to 85° C. for 2 hours. 80 ml of butyl acetate and 80 ml of water were added to the reaction solution, and the mixture was partitioned. 5.68 g (58.5 mmol) of sulfamic acid and 10 ml of water were added to the organic layer, and 21.15 g (58.5 mmol) of a 25% sodium chlorite aqueous solution was added dropwise thereto at 20° C. or below, followed by reaction for 15 minutes. 10 ml of a 25% sodium hydroxide aqueous solution was added thereto at 20° C. or below, and subsequently 80.41 g (63.8 mmol) of a 10% sodium sulfite aqueous solution was poured in. Additionally, 2 ml of concentrated hydrochloric acid was added, and the mixture was partitioned, followed by concentration of the organic layer under reduced pressure. 40 ml of methanol, 80 ml of water, and 10 ml of a 25% sodium hydroxide aqueous solution were added to the concentrated residue, and the residue was dissolved, followed by dropwise addition of 5 ml of concentrated hydrochloric acid to precipitate crystals. The precipitated crystals were collected by filtration and dried at 80° C., thereby obtaining 12.09 g (yield: 92.4%) of compound (3) as a white powder.

Production Example 3: Production of Compound (7)

Compound (7) was produced in accordance with the following reaction scheme.

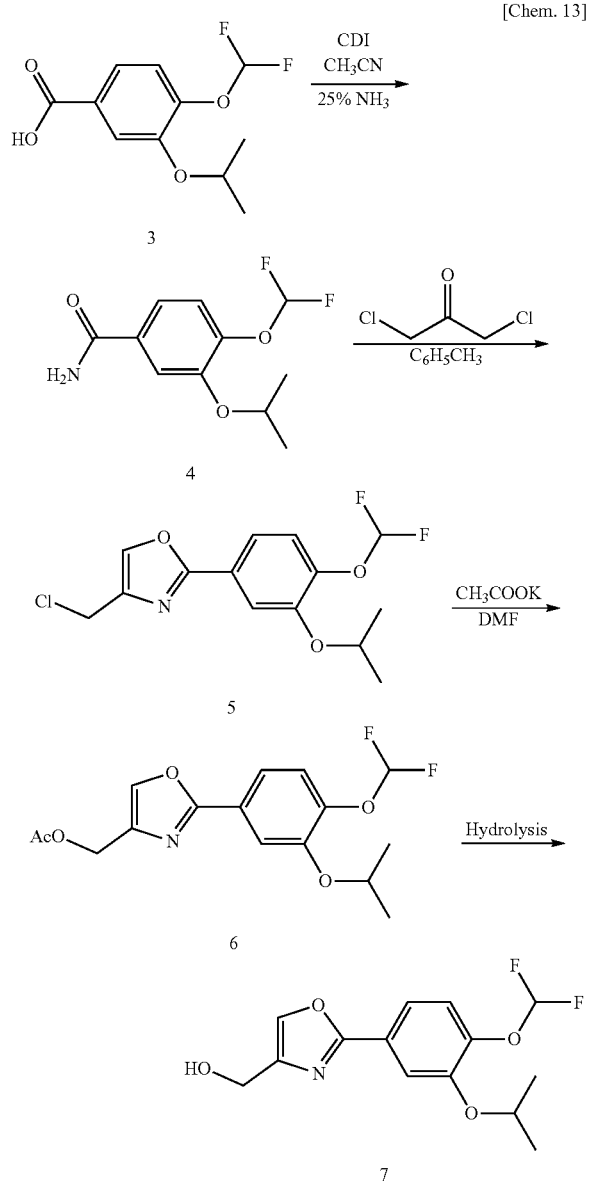

Synthesis of Compound (4)

10.00 g (40.6 mmol) of compound (3) was added to 25 ml of acetonitrile at room temperature and stirred. 7.90 g (48.7 mmol) of carbonyl diimidazole was gradually added, and the mixture was reacted at room temperature for 1 hour. 10 ml (134 mmol) of 25% ammonia water was added to 120 ml of water and cooled to 10° C. or below, followed by dropwise addition of the reaction solution thereto. The precipitated crystals were collected by filtration and dried at 80° C., thereby obtaining 9.25 g (yield: 92.9%) of compound (4) as a white powder.

$^1$H-NMR (CDCl$_3$) δ: 7.54 (1H, d, J=1.6 Hz), 7.25 (1H, dd, J=8.4 Hz, 2.0 Hz), 7.17 (1H, d, J=8.0 Hz), 6.62 (1H, t, J=75.0), 5.96 (2H, br-d, J=75.2 Hz), 4.66 (1H, sept, J=6.13 Hz), 1.36 (6H, d, J=6.0 Hz).

Synthesis of Compound (5)

10.00 g (40.8 mmol) of compound (4) and 6.21 g (48.9 mmol) of 1,3-dichloroacetone were added to 10 ml of toluene at room temperature, and the mixture was reacted under reflux for 3 hours. 60 ml of toluene, 20 ml of water, and 2 ml of a 25% sodium hydroxide aqueous solution were added to the reaction solution, and the mixture was partitioned. The organic layer was concentrated under reduced pressure, thereby obtaining compound (5) as a brownish solid (after recrystallization: fine yellow powder).

$^1$H-NMR (CDCl$_3$) δ: 7.69 (1H, d, J=0.8 Hz), 7.64 (1H, d, J=2.0 Hz), 7.58 (1H, dd, J=8.0 Hz, 1.6 Hz), 7.21 (1H, d, J=8.0 Hz), 6.61 (1H, t, J=75.0 Hz), 4.69 (1H, sept, J=6.1 Hz), 4.56 (2H, s), 1.38 (6H, d, J=6.0 Hz).

Synthesis of Compound (7)

20 ml of N,N-dimethylformamide and 4.80 g (48.9 mmol) of potassium acetate were added to the crude product of compound (5) obtained in the section above, and the mixture was reacted at 90 to 100° C. for 3 hours. 20 ml of methanol, 20 ml of water, and 5 ml of a 25% sodium hydroxide aqueous solution were added to the reaction solution, and reacted under reflux for 1 hour. 35 ml of water was added to the reaction solution, and the precipitated crystals were collected by filtration, followed by drying at 80° C., thereby obtaining 10.33 g (yield: 84.6%) of compound (7) as a pale brownish powder.

$^1$H-NMR (CDCl$_3$) δ: 7.65-7.63 (2H, m), 7.57 (1H, dd, J=8.4 Hz, 2.0 Hz), 7.21 (1H, d, J=8.0 Hz), 6.61 (1H, t, J=75.2 Hz), 4.70-4.66 (3H, m), 1.39 (6H, d, J=6.0 Hz).

Production Example 4: Production of Compound (11)

Compound (11) was produced in accordance with the following reaction scheme.

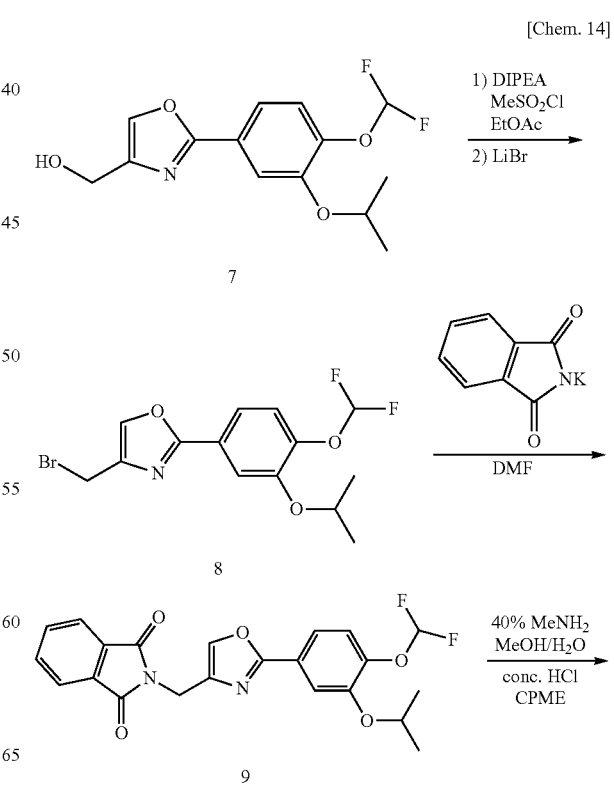

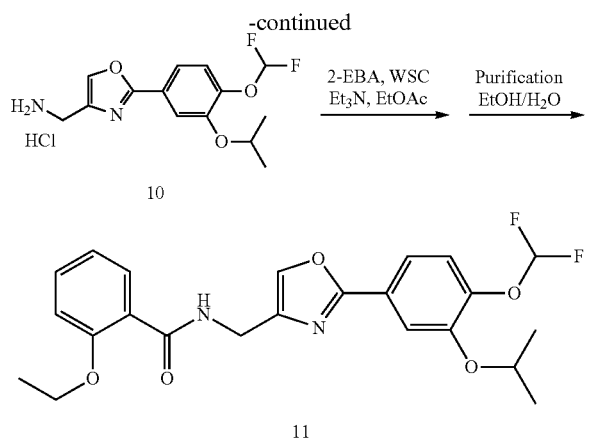

Synthesis of Compound (9)

20.00 g (66.8 mmol) of compound (7) and 17.28 g (134 mmol) of N,N-diisopropylethylamine were added to 300 ml of ethyl acetate, and the mixture was cooled. 11.48 g (100 mmol) of methanesulfonyl chloride was poured in and stirred at 10 to 30° C. for 1 hour. 17.41 g (200 mmol) of lithium bromide was added thereto and reacted at 20 to 35° C. for 1 hour. 100 ml of water was added to the reaction solution, and the mixture was partitioned, followed by concentration of the organic layer under reduced pressure. 300 ml of ethyl acetate was added to the concentrated residue to dissolve the residue, and the solution was again concentrated under reduced pressure. 200 ml of N,N-dimethylformamide and 17.33 g (93.6 mmol) of potassium phthalimide were added to the concentrated residue and reacted at 75 to 85° C. for 1 hour. 200 ml of water was added to the reaction solution to precipitate crystals. The precipitated crystals were collected by filtration and dried at 80° C., thereby obtaining 25.90 g (yield: 90.5%) of compound (9) as a white powder.

$^1$H-NMR (DMSO-$d_6$) δ: 8.22 (1H, s), 7.94-7.86 (4H, m), 7.58 (1H, d, J=2.0 Hz), 7.52 (1H, dd, J=8.8 Hz, 2.4 Hz), 7.30 (1H, d, J=8.4 Hz), 7.14 (1H, t, J=74.2 Hz), 4.78-4.69 (3H, m), 1.30 (6H, d, J=6.0 Hz).

Synthesis of Compound (10)

15.00 g (35.0 mmol) of compound (9) was mixed with 30 ml of a 40% methylamine aqueous solution, 30 ml of methanol, and 75 ml of water, and reacted under reflux for 30 minutes. 150 ml of cyclopentyl methyl ether (CPME) and 15 ml of a 25% sodium hydroxide aqueous solution were added to the reaction solution, and the temperature was adjusted to 65 to 75° C., followed by partitioning. A mixture of 150 ml of water and 7.50 g of sodium chloride was added to the organic layer, and the temperature was adjusted to 65 to 75° C. again, followed by partitioning. 3.75 ml of concentrated hydrochloric acid was added to the organic layer to precipitate crystals. The precipitated crystals were collected by filtration and dried at 60° C., thereby obtaining 11.95 g (yield: quant.) of compound (10) as a white powder.

$^1$H-NMR (DMSO-$d_6$) δ: 8.51 (3H, br-s), 8.29 (1H, s), 7.64 (1H, d, J=2 Hz), 7.59 (1H, dd, J=8.0 Hz, 1.6 Hz), 7.37 (1H, d, J=8.4 Hz), 7.18 (1H, t, J=74.0 Hz), 4.72 (1H, sept, J=6.1 Hz), 4.03 (2H, s), 1.33 (6H, d, J=6.4 Hz).

Synthesis of Compound (11)

13.30 g (39.7 mmol) of compound (10) was mixed with 3.83 g (37.8 mmol) of triethylamine and 108 ml of ethyl acetate, and stirred at 20 to 30° C. for 1 hour. 9.78 g (58.9 mmol) of 2-ethoxybenzoic acid and 11.28 g (58.8 mmol) of 1-ethyl-3-(3-dimethylaminopropyl)carbodiimide hydrochloride (WSC) were added to the reaction solution, and reacted at 20 to 30° C. for 1 hour. 54 ml of water and 5.4 ml of concentrated hydrochloric acid were added to the reaction solution, and the temperature was adjusted to 40 to 50° C., followed by partitioning. 54 ml of water and 5.4 ml of a 25% sodium hydroxide aqueous solution were added to the organic layer, and the temperature was adjusted to 40 to 50° C. again. The mixture was partitioned, and the organic layer was concentrated under reduced pressure. 45 ml of ethanol, 18 ml of water, 5.4 ml of a 25% sodium hydroxide aqueous solution, and 0.54 g of activated carbon were added to the concentrated residue, and the mixture was refluxed for 30 minutes. The activated carbon was removed by filtration, and the filtrate was washed with 11 ml of ethanol. The filtrate was cooled, and a seed crystal was added thereto to precipitate crystals. The precipitated crystals were collected by filtration and dried at 35° C., thereby obtaining 12.88 g (72.6%) of compound (11) as a white powder.

$^1$H-NMR (CDCl$_3$) δ: 8.56 (1H, br-s), 8.23 (1H, dd, J=7.6 Hz, 1.6 Hz), 7.66 (1H, s), 7.63 (1H, d, J=2.0 Hz), 7.58 (1H, dd, J=8.4 Hz, 2.0 Hz), 7.44-7.39 (1H, m), 7.21 (1H, d, J=8.0 Hz), 7.08-7.04 (1H, mH), 6.94 (1H, d, J=8.0 Hz), 6.61 (1H, t, J=75.2 Hz), 4.68 (1H, sept, J=6.0 Hz), 4.62 (2H, d, J=6.0 Hz), 4.17 (2H, q, J=6.93), 1.48 (3H, t, J=7.2 Hz), 1.39 (6H, d, J=5.6 Hz).

Production Example 5: Production of Compounds (i) to (ix)

The compounds shown in the following Table 2 were produced as described below. The $^1$H-NMR of the produced compounds is also shown below. Compound (ii) is the same as compound (9).

TABLE 2

| Formula Number | Structural Formula |
|---|---|
| i | ![structure] |

TABLE 2-continued
| Formula Number | Structural Formula |
|---|---|
| ii | 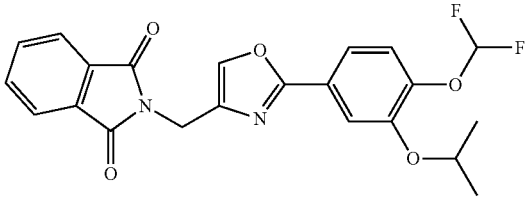 [SMILES: CC(C)Oc1cc(-c2nc(CN3C(=O)c4ccccc4C3=O)co2)ccc1OC(F)F] |
| iii | 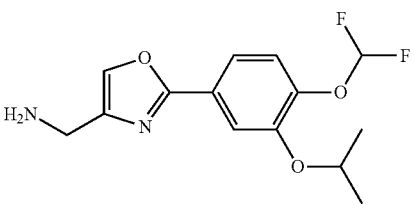 [SMILES: CC(C)Oc1cc(-c2nc(CN)co2)ccc1OC(F)F] |
| iv | 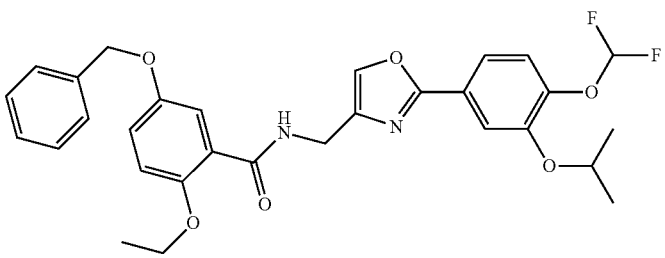 [SMILES: CCOc1ccc(OCc2ccccc2)cc1C(=O)NCc1coc(-c2ccc(OC(F)F)c(OC(C)C)c2)n1] |
| v | 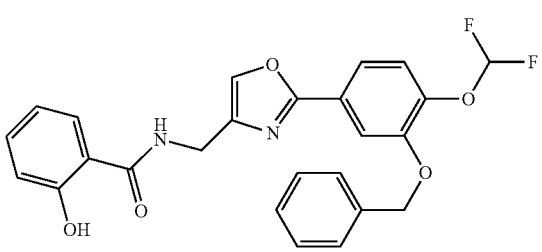 [SMILES: O=C(NCc1coc(-c2ccc(OC(F)F)c(OCc3ccccc3)c2)n1)c1ccccc1O] |
| vi | 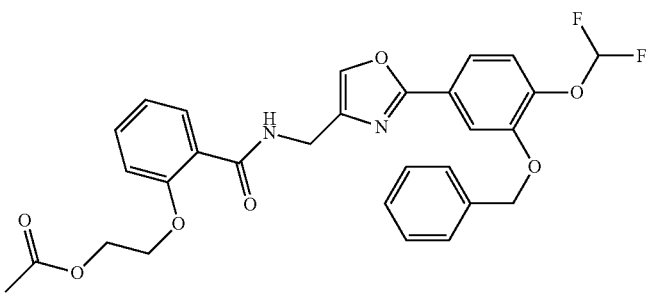 [SMILES: CC(=O)OCCOc1ccccc1C(=O)NCc1coc(-c2ccc(OC(F)F)c(OCc3ccccc3)c2)n1] |
| vii | 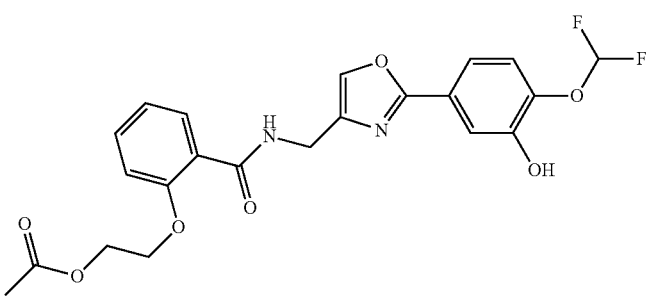 [SMILES: CC(=O)OCCOc1ccccc1C(=O)NCc1coc(-c2ccc(OC(F)F)c(O)c2)n1] |

TABLE 2-continued

| Formula Number | Structural Formula |
|---|---|
| viii | *(structure: methyl 2-(4-(difluoromethoxy)-3-(benzyloxy)phenyl)oxazole-4-carboxylate)* |
| ix | *(structure: methyl 2-(4-(difluoromethoxy)-3-hydroxyphenyl)oxazole-4-carboxylate)* |

Synthesis of Compound (i)

13.1 g of 2-[2-(3-benzyloxy-4-difluoromethoxyphenyl) oxazol-4-ylmethyl]isoindoline-1,3-dione(2-((2-(3-(benzyloxy)-4-(difluoromethoxy)phenyl)oxazol-4-yl)methyl) isoindoline-1,3-dione) synthesized in accordance with the synthesis procedure described in PTL 2 (WO2014/034958 pamphlet) was dissolved in a mixture of 260 ml of ethanol and 140 ml of DMF, and 1.3 g of a 10% palladium carbon powder was added thereto, followed by stirring in a hydrogen atmosphere at 40° C. for 1 hour. 100 ml of methylene chloride was added to the reaction solution and stirred, followed by removal of the catalyst by filtration. The crude crystals obtained by concentrating the filtrate were recrystallized from ethyl acetate, thereby obtaining 8.8 g of 2-[2-(4-difluoromethoxy-3-hydroxyphenyl)oxazol-4-ylmethyl]isoindoline-1,3-dione (2-((2-(4-(difluoromethoxy)-3-hydroxyphenyl)oxazol-4-yl)methyl)isoindoline-1,3-dione: compound (i)) as a white powder.

$^1$H-NMR (CDCl$_3$) δ: 8.18 (1H, br-s) 7.85-8.17 (5H, m) 6.89-7.51 (4H, m) 4.74 (2H, s).

Synthesis of Compound (ii)

2 g of compound (i) and 3.9 ml of 1,8-diazabicyclo[5,4,0]undec-7-ene (DBU) were dissolved in 20 ml of ethanol, and 3.18 g of isopropyl bromide was added thereto, followed by heating under reflux overnight. Subsequently, 1 ml of a 10% sodium hydroxide aqueous solution was added to the reaction solution, and the mixture was heated under reflux for 30 minutes. Ice water was added to the reaction solution, followed by extraction with ethyl acetate. The organic layer was washed with water twice, and concentrated under reduced pressure, thereby obtaining [2-(3-isopropoxy-4-difluoromethoxyphenyl)oxazol-4-ylmethyl]isoindoline-1,3-dione (2-((2-(4-(difluoromethoxy)-3-isopropoxyphenyl)oxazol-4-yl)methyl)isoindoline-1,3-dione: compound (ii)).

$^1$H-NMR (CDCl$_3$) δ: 7.85-7.92 (2H, m) 7.71-7.77 (2H, m) 7.68 (1H, s) 7.61 (1H, d, J=2.1 Hz) 7.55 (1H, dd, J=8.4 Hz, 2.1 Hz) 7.18 (1H, d, J=8.4 Hz) 6.60 (1H, t, J=75 Hz) 4.86 (2H, d, J=1.2 Hz) 4.68 (1H, sept, J=6.0 Hz) 1.38 (6H, d, J=6.0 Hz).

Synthesis of Compound (iii)

1.58 g of compound (ii) was dissolved in 16 ml of methanol, and 3.2 ml of a methylamine aqueous solution (40%) was added thereto, followed by heating under reflux for 1 hour. The reaction solution was concentrated, and the reaction product was dissolved in ethyl acetate, followed by washing of the organic layer with a 10% sodium hydroxide aqueous solution and water. The organic layer was separated and concentrated under reduced pressure, thereby obtaining 1.17 g of [2-(4-difluoromethoxy-3-isopropoxyphenyl)oxazol-4-yl]methylamine ((2-(4-(difluoromethoxy)-3-isopropoxyphenyl)oxazol-4-yl)methanamine: compound (iii)) as a brownish solid.

$^1$H-NMR (CDCl$_3$) δ: 7.65 (1H, d, J=1.8 Hz) 7.58 (1H, d, J=8.4 Hz, 1.8 Hz) 7.55 (1H, s) 7.22 (1H, d, J=8.4 Hz) 6.62 (1H, t, J=75 Hz) 4.70 (1H, sept, J=6.3 Hz) 3.85 (2H, s) 1.40 (6H, d, J=6.3 Hz).

Synthesis of Compound (iv)

0.24 g of 5-benzyloxy-2-ethoxybenzoic acid and 0.44 g of compound (iii) were suspended in 20 ml of acetone, and 0.27 g of 1-hydroxy benzotriazole (HOBt) and 0.38 g of 1-ethyl-3-(3-dimethylaminopropyl)carbodiimide hydrochloride (WSC) were added thereto, followed by heating under reflux for 1 hour. The reaction solution was cooled, and acetone was evaporated under reduced pressure, followed by addition of water to the residue and extraction with ethyl acetate. The organic layer was washed with water twice and concentrated under reduced pressure. The obtained residue was purified by silica gel column chromatography (n-hexane:ethyl acetate=3:1). The obtained crude crystals were recrystallized from n-hexane:ethyl acetate, thereby obtaining 0.28 g of N-[2-(4-difluoromethoxy-3-isopropoxyphenyl)oxazol-4-ylmethyl]-5-benzyloxy-2-ethoxybenzamide (5-(benzyloxy)-N-((2-(4-(difluoromethoxy)-3-isopropoxyphenyl)oxazol-4-yl)methyl)-2-ethoxybenzamide: compound (iv)) as a white powder.

$^1$H-NMR (CDCl$_3$) δ: 8.68 (1H, br-s), 7.76 (1H, d, J=3 Hz), 7.66-7.57 (3H, m), 7.38-7.20 (6H, m), 6.97 (1H, dd, J=3.3, 8.7 Hz), 6.62 (1H, t, J=75 Hz), 4.71-4.61 (4H, m), 4.05 (2H, q, J=6.9 Hz), 1.57-1.37 (9H, m).

Synthesis of Compound (v)

5.5 g of [2-(3-benzyloxy-4-difluoromethoxyphenyl)oxazol-4-yl]methylamine(2-(3-(benzyloxy)-4-(difluoromethoxy)phenyl)oxazol-4-yl)methanamine (MAP-15211) synthesized in accordance with the synthesis procedure described in PTL 2 (WO2014/034958 pamphlet) and 3.4 g of acetylsalicylic acid were suspended in 150 ml of acetone.

3.4 g of 1-hydroxy benzotriazole (HOBt) and 4.8 g of 1-ethyl-3-(3-dimethylaminopropyl)carbodiimide hydrochloride (WSC) were added thereto, followed by heating under reflux for 1 hour. Subsequently, 10 ml of a 10% sodium hydroxide aqueous solution was added thereto, and the mixture was heated under reflux for 30 minutes. The reaction solution was then cooled, and acetone was evaporated under reduced pressure. Water was added to the residue and extraction was performed with ethyl acetate. The organic layer was washed with water twice and concentrated under reduced pressure, thereby obtaining 3.1 g of N-[2-(3-benzyloxy-4-difluoromethoxyphenyl)oxazol-4-ylmethyl]-2-hydroxybenzamide (N-((2-(3-(benzyloxy)-4-(difluoromethoxy)phenyl)oxazol-4-yl)methyl)-2-hydroxybenzamide: compound (v)) as a white powder.

$^1$H-NMR (CDCl$_3$) δ: 12.19 (1H, s) 7.70-7.72 (2H, m), 7.63 (1H, dd, J=8.4, 1.8 Hz), 7.28-7.51 (7H, m), 7.22-7.26 (2H, m), 6.98-7.01 (1H, m), 6.82-6.88 (2H, m), 6.63 (1H, t, J=74.7 Hz), 5.22 (2H, s), 4.60 (2H, dd, J=5.4, 0.9 Hz).

Synthesis of Compound (vi)

3.1 g of compound (v) was dissolved in 45 ml of N,N-dimethylformamide, and 1.7 g of 2-bromoethyl acetate and 1.8 g of potassium carbonate were added thereto, followed by heating with stirring at 80° C. for 1 hour. Ice water was added to the reaction solution, and extraction was performed with ethyl acetate. The organic layer was washed with water twice and concentrated under reduced pressure. The obtained residue was purified by silica gel column chromatography (ethyl acetate:n-hexane=1:1), thereby obtaining 3.6 g of N-[2-(3-benzyloxy-4-difluoromethoxyphenyl)oxazol-4-ylmethyl]-2-[(2-acetoxy)ethoxy]benzamide (2-(2-((2-(3-(benzyloxy)-4-(difluoromethoxy)phenyl)oxazol-4-yl)methylcarbamoyl)phenoxy)ethyl acetate: compound (vi)) as a white powder.

$^1$H-NMR (CDCl$_3$) δ: 8.43 (1H, br-s) 8.25 (1H, d, J=8.4 Hz), 7.73 (1H, d, J=1.8 Hz), 7.68 (1H, s), 7.62 (1H, dd, J=5.4, 1.8 Hz), 7.34-7.49 (6H, m), 7.24-7.26 (1H, m), 7.09-7.15 (1H, m), 6.93 (1H, d, J=7.8 Hz), 6.63 (1H, t, J=74.4 Hz), 5.22 (2H, s), 4.65 (2H, d, J=5.7 Hz), 4.50-4.53 (2H, m), 4.27-4.32 (2H, m), 2.03 (3H, S).

Synthesis of Compound (vii)

3.5 g of compound (vi) was suspended in 100 ml of ethanol, and 0.4 g of a 10% palladium carbon powder was added thereto, followed by stirring in a hydrogen atmosphere at room temperature for 4 hours. The catalyst was removed by filtration, and the crude crystals obtained by concentrating the filtrate were recrystallized from ethanol-n-hexane, thereby obtaining 2.1 g of N-[2-(3-hydroxy-4-difluoromethoxyphenyl)oxazol-4-ylmethyl]-2-[(2-acetoxy)ethoxy]benzamide (2-(2-((2-(4-(difluoromethoxy)-3-hydroxyphenyl)oxazol-4-yl)methylcarbamoyl)phenoxy)ethyl acetate: compound (vii)) as a white powder.

$^1$H-NMR (CDCl$_3$) δ: 8.45 (1H, br-s), 8.25 (1H, d, J=8.4 Hz), 7.76 (1H, s), 7.66 (1H, s), 7.42-7.53 (2H, m), 7.09-7.26 (3H, m), 6.95 (1H, d, J=7.8 Hz), 6.78 (1H, br-s), 6.64 (1H, t, J=74.1 Hz), 4.58-4.65 (4H, m), 4.31-4.34 (2H, m), 2.11 (2H, s).

Synthesis of Compound (viii)

5.1 g of methyl pyruvate and 0.8 ml of bromine were dissolved in 15 ml of 1,2-dimethoxyethane, and the solution was heated with stirring at 50° C. for 1 hour. The reaction solution was concentrated, and the residue was dissolved in 45 ml of 2-methoxy ethanol. 3 g of 3-benzyloxy-4-difluoromethoxybenzamide (3-(benzyloxy)-4-(difluoromethoxy)benzamide) synthesized in accordance with the synthesis procedure described in PTL 1 (WO2007/058338 pamphlet) was added thereto and heated under reflux for 4 hours. 25 ml of water was added to the reaction solution and stirred at room temperature overnight. The precipitated crystals were collected by filtration and dried under reduced pressure at room temperature, thereby obtaining 0.73 g of methyl 2-(3-benzyloxy-4-difluoromethoxyphenyl)oxazole-4-carboxylate (methyl 2-(3-(benzyloxy)-4-(difluoromethoxy)phenyl)oxazole-4-carboxylate: compound (viii)) as white crystals.

$^1$H-NMR (CDCl$_3$) δ: 8.29 (1H, s) 7.84 (1H, d, J=2.1 Hz) 7.71 (1H, dd, J=8.4 Hz, 1.8 Hz) 7.35-7.48 (6H, m) 6.64 (1H, t, J=75 Hz) 5.22 (2H, s) 3.97 (3H, s).

Synthesis of Compound (ix)

0.28 g of compound (viii) was dissolved in 5 ml of ethanol, 1 ml of tetrahydrofuran, and 0.5 ml of N,N-dimethylformamide, and 0.03 g of a 10% palladium carbon powder was added thereto, followed by stirring in a hydrogen atmosphere at room temperature for 2 hours. The catalyst was removed by filtration, and the filtrate was concentrated under reduced pressure. Water was added to the residue, and extraction was performed with ethyl acetate. The organic layer was washed with a saturated sodium chloride solution one time and concentrated under reduced pressure, thereby obtaining 0.18 g of methyl 2-(3-hydroxy-4-difluoromethoxyphenyl)oxazole-4-carboxylate (methyl 2-(4-(difluoromethoxy)-3-hydroxyphenyl)oxazole-4-carboxylate: compound (ix)) as white crystals.

$^1$H-NMR (CDCl$_3$) δ: 8.28 (1H, s), 7.77 (1H, d, J=1.8 Hz), 7.68 (1H, dd, J=8.4, 1.8 Hz), 7.21 (1H, d, J=8.4 Hz), 6.61 (1H, t, J=72.9 Hz), 5.57 (1H, s), 3.96 (3H, s).

Production Example 6: Production of Compounds (11a) to (11s)

The compounds shown in the following Table 3 were produced as described below. The $^1$H-NMR of the produced compounds is also shown below.

TABLE 3

| Formula Number | Structural Formula |
|---|---|
| 11a |  |

TABLE 3-continued

| Formula Number | Structural Formula |
|---|---|
| 11b | (structure) |
| 11c | (structure) |
| 11d | (structure) |
| 11e | (structure) |
| 11f | (structure) |
| 11g | (structure) |
| 11h | (structure) |

TABLE 3-continued

| Formula Number | Structural Formula |
|---|---|
| 11i | (structure) |
| 11j | (structure) |
| 11k | (structure) |
| 11l | (structure) |
| 11m | (structure) |
| 11n | (structure) |
| 11o | (structure) |

TABLE 3-continued

| Formula Number | Structural Formula |
|---|---|
| 11p | *(structure)* |
| 11q | *(structure)* |
| 11r | *(structure)* |
| 11s | *(structure)* |

Synthesis of Compound (11a)

3 g of compound (iii) and 1.5 g of salicylic acid were suspended in 60 ml of acetone, and 1.8 g of 1-hydroxy benzotriazole (HOBt) and 2.6 g of 1-ethyl-3-(3-dimethylaminopropyl)carbodiimide hydrochloride (WSC) were added thereto, followed by heating under reflux for 1 hour. The reaction solution was cooled, and acetone was evaporated under reduced pressure. Water was added to the residue, and extraction was performed with ethyl acetate. The organic layer was washed with water twice and concentrated under reduced pressure. The obtained crude crystals were recrystallized from ethyl acetate-n-hexane, thereby obtaining 1.47 g of N-[2-(3-isopropoxy-4-difluoromethoxyphenyl)oxazol-4-ylmethyl]-2-hydroxybenzamide (N-((2-(4-(difluoromethoxy)-3-isopropoxyphenyl)oxazol-4-yl)methyl)-2-hydroxybenzamide: compound (11a)) as a white powder.

$^1$H-NMR (CDCl$_3$) δ: 12.19 (1H, s), 7.70 (1H, s), 7.50-7.64 (2H, m), 7.37-7.42 (2H, m), 7.23 (1H, d, J=8.4 Hz), 6.81-7.01 (3H, m), 6.63 (1H, t, J=75.0 Hz), 4.69 (1H, sept., J=6.0 Hz), 4.59 (2H, d, J=5.4 Hz), 1.40 (6H, d, J=6.0 Hz).

Synthesis of Compound (11b)

The procedure in "Synthesis of Compound (11a)" above was repeated using 0.44 g of compound (iii) and 0.24 g of 2-ethoxy-3-hydroxy benzoic acid, thereby obtaining 0.28 g of N-[2-(3-isopropoxy-4-difluoromethoxyphenyl) oxazol-4-ylmethyl]-2-ethoxy-3-hydroxybenzamide (N-((2-(4-(difluoromethoxy)-3-isopropoxyphenyl)oxazol-4-yl)methyl)-2-ethoxy-3-hydroxybenzamide: compound (11b)) as a white powder.

¹H-NMR (CDCl₃) δ: 7.97 (1H, br-t, J=5.1 Hz), 7.70 (1H, s), 7.64 (1H, d, J=1.8 Hz), 7.52-7.60 (3H, m), 7.23 (1H, d, J=8.4 Hz), 7.10 (1H, d, J=2.4 Hz), 7.09 (1H, s), 6.63 (1H, t, J=75.0 Hz), 4.64-4.72 (1H, m), 4.61 (2H, d, J=5.1 Hz), 4.00 (2H, q, J=6.9 Hz), 1.38 (3H, t, J=6.9 Hz).

Synthesis of Compound (11c)

The procedure in "Synthesis of Compound (11a)" above was repeated using compound (iv), thereby obtaining 5 mg of N-[2-(3-isopropoxy-4-difluoromethoxyphenyl) oxazol-4-ylmethyl]-2-ethoxy-5-hydroxybenzamide (N-((2-(4-(difluoromethoxy)-3-isopropoxyphenyl)oxazol-4-yl)methyl)-2-ethoxy-5-hydroxybenzamide: compound (11c)) as a white powder.

¹H-NMR (CDCl₃) δ: 8.83 (1H, br), 8.04 (1H, d, J=3.3 Hz), 7.69 (1H, s), 7.64 (1H, d, J=1.8 Hz), 7.58 (1H, dd, J=1.8, 8.4 Hz), 7.21 (1H, d, J=5.1 Hz), 6.87-6.99 (3H, m), 6.62 (1H, t, J=75 Hz), 4.61-4.72 (3H, m), 4.12 (2H, q, J=6.9 Hz), 1.38-1.47 (9H, m)

Synthesis of Compound (11d)

0.1 g of compound (11a) was dissolved in 3 ml of N,N-dimethylformamide, and 0.12 g of 2-bromoethyl acetate and 0.14 g of potassium carbonate were added thereto, followed by heating with stirring at 80° C. for 2 hours. Subsequently, 1 ml of methanol and 0.3 ml of a 25% sodium hydroxide aqueous solution were added to the reaction solution, and the mixture was heated under reflux for 1 hour. Ice water was added to the reaction solution, and extraction was performed with ethyl acetate. The organic layer was washed with water twice and concentrated under reduced pressure. The obtained residue was recrystallized from ethyl acetate-n-hexane, thereby obtaining 70 mg of N-[2-(3-isopropoxy-4-difluoromethoxyphenyl)oxazol-4-ylmethyl]-2-(2-hydroxyethoxy) benzamide (N-((2-(4-(difluoromethoxy)-3-isopropoxyphenyl) oxazol-4-yl)methyl)-2-(2-hydroxyethoxy)benzamide: compound (11d)) as a white powder.

¹H-NMR (CDCl₃) δ: 8.67 (1H, br-s) 8.16 (1H, dd, J=7.8, 1.8 Hz), 7.70-7.74 (2H, m), 7.62 (1H, dd, J=8.4, 1.8 Hz), 7.40-7.46 (1H, m), 7.24-7.26 (1H, m), 7.06-7.12 (1H, m), 6.94-6.97 (1H, m), 6.65 (1H, t, J=75.0 Hz), 5.43 (1H, t, J=6.6 Hz), 4.69-4.77 (1H, m), 4.62 (2H, d, J=5.4 Hz), 4.18-4.21 (2H, m), 3.94-3.99 (2H, m), 1.42 (6H, d, J=6.3 Hz).

Synthesis of Compound (11e)

0.3 g of compound (vii) and 0.3 ml of 1,8-diazabicyclo[5,4,0]undec-7-ene (DBU) were dissolved in 4 ml of ethanol, and 0.31 g of ethyl iodide was added thereto, followed by heating under reflux overnight. Subsequently, 1 ml of a 10% sodium hydroxide aqueous solution was added to the reaction solution, and heated under reflux for 30 minutes. Thereafter, ice water was added to the reaction solution, and extraction was performed with ethyl acetate. The organic layer was washed with water twice and concentrated under reduced pressure. The obtained crude crystals were recrystallized from ethanol-n-hexane, thereby obtaining 95 mg of N-[2-(3-ethoxy-4-difluoromethoxyphenyl)oxazol-4-ylmethyl]-2-(2-hydroxyethoxy)benzamide N-((2-(4-(difluoromethoxy)-3-ethoxyphenyl)oxazol-4-yl)methyl)-2-(2-hydroxyethoxy)benzamide (OPA-15566) as a white powder.

¹H-NMR (CDCl₃) δ: 8.86 (1H, br-s) 8.15 (1H, dd, J=8.1, 1.8 Hz), 7.74 (1H, d, J=2.1 Hz), 7.70 (1H, s), 7.63 (1H, dd, J=8.1, 2.1 Hz), 7.40-7.46 (2H, m), 7.06-7.09 (1H, m), 6.90-6.96 (1H, m), 6.66 (1H, t, J=74.7 Hz), 5.45 (1H, brs), 4.62 (2H, d, J=5.4 Hz), 4.22 (2H, q, J=6.9 Hz), 4.19 (2H, dd, J=4.5, 4.2 Hz), 3.97 (2H, dd, J=4.5, 4.2 Hz), 1.50 (3H, t, J=6.9 Hz)

Synthesis of Compound (11f)

0.3 g of compound (vii) and 0.3 ml of 1,8-diazabicyclo[5,4,0]undec-7-ene (DBU) were dissolved in ethanol, and 0.27 g of (bromomethyl)cyclopropane was added thereto, followed by heating under reflux overnight. Subsequently, 1 ml of a 10% sodium hydroxide aqueous solution was added to the reaction solution, and heated under reflux for 30 minutes. Ice water was then added to the reaction solution, and extraction was performed with ethyl acetate. The organic layer was washed with water twice and concentrated under reduced pressure. The obtained residue was purified by silica gel column chromatography (methylene chloride). The obtained crude crystals were recrystallized from ethyl acetate-n-hexane, thereby obtaining 0.26 g of N-[2-(3-cyclopropyl methoxy-4-difluoromethoxyphenyl)oxazol-4-ylmethyl]-2-(2-hydroxyethoxy)benzamide (N-((2-(3-(cyclopropylmethoxy)-4-(difluoromethoxy)phenyl) oxazol-4-yl)methyl)-2-(2-hydroxyethoxy)benzamide: compound (11f)) as a white powder.

¹H-NMR (CDCl₃) δ: 8.85 (1H, br-s) 8.16 (1H, dd, J=7.5, 1.8 Hz), 7.61-7.73 (2H, m), 7.40-7.46 (1H, m), 7.24-7.27 (1H, m), 7.06-7.12 (1H, m), 6.72 (1H, t, J=74.7 Hz), 5.37-5.42 (1H, m), 4.18-4.21 (2H, m), 3.94-4.01 (4H, m), 1.32-1.37 (1H, m), 0.65-0.71 (2H, m), 0.37-042 (2H, m).

Synthesis of Compound (11g)

0.3 g of compound (vii) and 0.3 ml of 1,8-diazabicyclo[5,4,0]undec-7-ene (DBU) were dissolved in ethanol, and 0.28 g of isobutyl bromide was added thereto, followed by heating under reflux overnight. Subsequently, 1 ml of a 10% sodium hydroxide aqueous solution was added to the reaction solution and heated under reflux for 30 minutes. Ice water was then added to the reaction solution, and extraction was performed with ethyl acetate. The organic layer was washed with water twice and concentrated under reduced pressure. The obtained residue was purified by silica gel column chromatography (methylene chloride). The obtained crude crystals were recrystallized from ethyl acetate-n-hexane, thereby obtaining 0.15 g of N-[2-(3-isobutoxy-4-difluoromethoxyphenyl) oxazol-4-ylmethyl]-2-(2-hydroxyethoxy) benzamide (N-((2-(4-(difluoromethoxy)-3-isobutoxyphenyl)oxazol-4-yl)methyl)-2-(2-hydroxyethoxy) benzamide: compound (11g)) as a white powder.

¹H-NMR (CDCl₃) δ: 8.86 (1H, br-s) 8.16 (1H, dd, J=7.8, 1.8 Hz), 7.70-7.74 (2H, m), 7.61-7.64 (1H, m), 7.40-7.46 (1H, m), 7.24-7.26 (1H, m), 6.97-6.90 (1H, m), 6.64 (1H, t, J=75.0 Hz), 5.40 (1H, t, J=6.6 Hz), 4.62 (2H, d, J=5.4 Hz), 4.18-4.22 (2H, m), 3.90-4.00 (4H, m), 2.11-2.25 (1H, m), 1.08 (6H, d, J=6.9 Hz).

Synthesis of Compound (11h)

0.3 g of compound (vii) and 0.3 ml of 1,8-diazabicyclo[5,4,0]undec-7-ene (DBU) were dissolved in ethanol, and 0.3 g of (bromomethyl)cyclobutane was added thereto, followed by heating under reflux overnight. Subsequently, 1 ml of a 10% sodium hydroxide aqueous solution was added to the reaction solution and heated under reflux for 30 minutes. Ice water was then added to the reaction solution, and extraction was performed with ethyl acetate. The organic layer was washed with water twice and concentrated under reduced pressure. The obtained residue was purified by silica gel column chromatography (methylene chloride). The obtained crude crystals were recrystallized from ethyl acetate-n-hexane, thereby obtaining 0.24 g of N-[2-(3-cyclobutylmethoxy-4-difluoromethoxyphenyl)oxazol-4-ylmethyl]-2-(2-hydroxyethoxy) benzamide (N-((2-(3-(cyclobutylmethoxy)-4-(difluoromethoxy)phenyl)oxazol-4-yl)methyl)-2-(2-hydroxyethoxy) benzamide: compound (11h)) as a white powder.

$^1$H-NMR (CDCl$_3$) δ: 8.86 (1H, br-s) 8.16 (1H, dd, J=7.8, 1.8 Hz), 7.63 (1H, dd, J=8.4, 2.1 Hz), 7.70-7.74 (2H, m), 7.40-7.46 (1H, m), 7.23-7.26 (1H, m), 7.07-7.12 (1H, m), 6.95 (1H, d, J=7.8 Hz), 6.65 (1H, t, J=75.3 Hz), 5.41 (1H, t, J=6.6 Hz), 4.62 (2H, d, J=5.4 Hz), 4.20 (2H, dd, J=4.5, 4.2 Hz), 4.11 (2H, d, J=6.6 Hz), 3.96-4.01 (2H, m), 2.80-2.90 (1H, m), 2.13-2.20 (2H, m), 1.88-2.02 (4H, m).

Synthesis of Compound (11i)

0.28 g of compound (iii) and 0.17 g of 2,3-dihydroxy benzoic acid were suspended in 3 ml of acetone, and 0.17 g of 1-hydroxy benzotriazole (HOBt) and 0.23 g of 1-ethyl-3-(3-dimethylaminopropyl)carbodiimide hydrochloride (WSC) were added thereto, followed by heating under reflux for 3 hours. The reaction solution was cooled, and acetone was evaporated under reduced pressure. Water was added to the residue, and extraction was performed with ethyl acetate. The organic layer was washed with water twice and concentrated under reduced pressure. The obtained residue was partially purified by silica gel column chromatography (dichloromethane:methanol=50:1). The obtained crude crystals were recrystallized from n-hexane-acetone, thereby obtaining 0.2 g of N-[2-(4-difluoromethoxy-3-isopropoxyphenyl)oxazol-4-ylmethyl]-2,3-dihydroxybenzamide (N-((2-(4-(difluoromethoxy)-3-isopropoxyphenyl) oxazol-4-yl)methyl)-2,3-dihydroxybenzamide: compound (11i)) as a white powder.

$^1$H-NMR (DMSO) δ: 12.54 (1H, s), 9.30 (1H, br-t, J=5.4 Hz), 9.23 (1H, s), 8.12 (1H, s), 7.61 (1H, d, J=1.8 Hz), 7.55 (1H, dd, J=8.4, 1.8 Hz), 7.38-7.28 (2H, m), 7.15 (1H, t, J=74.1 Hz), 6.95-6.89 (1H, m), 6.69 (1H, t, J=8.1 Hz), 4.74 (1H, sept., J=6.0 Hz), 4.45 (2H, d, J=5.4 Hz), 1.32 (6H, d, J=6.0 Hz).

Synthesis of Compound (11j)

The procedure in "Synthesis of Compound (11i)" above was repeated using 0.28 g of compound (iii) and 0.17 g of 2,4-dihydroxybenzoic acid, thereby obtaining 0.17 g of N-[2-(3-isopropoxy-4-difluoromethoxyphenyl) oxazol-4-ylmethyl]-2,4-dihydroxybenzamide (N-((2-(4-(difluoromethoxy)-3-isopropoxyphenyl)oxazol-4-yl)methyl)-2,4-dihydroxybenzamide: compound (11j)) as a white powder.

$^1$H-NMR (DMSO) δ: 12.75 (1H, s), 10.11 (1H, s), 9.05 (1H, br-t, J=5.4 Hz), 8.10 (1H, s), 7.74 (1H, d, J=8.7 Hz), 7.61 (1H, d, J=1.8 Hz), 7.55 (1H, dd, J=8.4, 1.8 Hz), 7.32 (1H, d, J=8.4 Hz), 7.16 (1H, t, J=74.1 Hz), 6.29 (1H, dd, J=8.7 Hz, 2.4 Hz), 6.24 (1H, d, J=2.4 Hz), 4.74 (1H, sept., J=6.0 Hz), 4.42 (2H, d, J=5.7 Hz), 1.32 (6H, d, J=6.0 Hz).

Synthesis of Compound (11k)

The procedure in "Synthesis of Compound (11i)" above was repeated using 0.28 g of compound (iii) and 0.17 g of 2,5-dihydroxybenzoic acid, thereby obtaining 0.16 g of N-[2-(3-isopropoxy-4-difluoromethoxyphenyl)oxazol-4-ylmethyl]-2,5-dihydroxybenzamide (N-((2-(4-(difluoromethoxy)-3-isopropoxyphenyl)oxazol-4-yl)methyl)-2,5-dihydroxybenzamide: compound (11k)) as a white powder.

$^1$H-NMR (DMSO) δ: 11.47 (1H, s), 9.14 (1H, br-t, J=5.4 Hz), 8.98 (1H, s), 8.08 (1H, s), 7.61 (1H, d, J=1.8 Hz), 7.55 (1H, dd, J=8.4, 1.8 Hz), 7.31 (1H, d, J=8.4 Hz), 7.29 (1H, d, J=3.0 Hz), 7.14 (1H, t, J=74.1 Hz), 6.86 (1H, dd, J=8.7 Hz), 6.74 (1H, d, J=8.7 Hz), 4.74 (1H, sept., J=6.0 Hz), 4.44 (2H, d, J=5.1 Hz), 1.31 (6H, d, J=6.0 Hz).

Synthesis of Compound (11l)

The procedure in "Synthesis of Compound (11i)" above was repeated using 0.28 g of compound (iii) and 0.17 g of 2,6-dihydroxybenzoic acid, thereby obtaining 0.2 g of N-[2-(3-isopropoxy-4-difluoromethoxyphenyl)oxazol-4-ylmethyl]-2,6-dihydroxybenzamide (N-((2-(4-(difluoromethoxy)-3-isopropoxyphenyl)oxazol-4-yl)methyl)-2,6-dihydroxybenzamide: compound (11l)) as a white powder.

$^1$H-NMR (DMSO) δ: 12.51 (1H, s), 9.32 (1H, br-t, J=5.4 Hz), 8.11 (1H, s), 7.62 (1H, d, J=1.8 Hz), 7.56 (1H, dd, J=8.4, 1.8 Hz), 7.32 (1H, d, J=8.4 Hz), 7.18 (1H, t, J=8.1 Hz), 7.14 (1H, t, J=74.1 Hz), 6.37 (2H, d, J=8.1 Hz), 4.74 (1H, sept., J=6.0 Hz), 4.52 (2H, d, J=5.4 Hz), 1.32 (6H, d, J=6.0 Hz).

Synthesis of Compound (11m)

0.2 g of compound (11a) was dissolved in 2 ml of acetonitrile. 0.23 g of sodium iodide, 0.27 g of potassium carbonate, and 98 mg of 3-chloropropyl acetate were added thereto, followed by heating under reflux overnight. 2 ml of a 10% sodium hydroxide aqueous solution was further added thereto, and the mixture was heated under reflux until the reaction was completed. After cooling, water was added to the reaction solution, and extraction was performed with ethyl acetate. The organic layer was washed with water twice and concentrated under reduced pressure. The obtained residue was purified by silica gel column chromatography (n-hexane:ethyl acetate=3:1), and the obtained crude crystals were recrystallized from ethanol-n-hexane, thereby obtaining 0.15 g of N-[2-(3-isopropoxy-4-difluoromethoxyphenyl)oxazol-4-ylmethyl]-2-(3-hydroxypropoxy)benzamide (N-((2-(4-(difluoromethoxy)-3-isopropoxyphenyl)oxazol-4-yl)methyl)-2-(3-hydroxypropoxy) benzamide: compound (11m)) as a white powder.

$^1$H-NMR (CDCl$_3$) δ: 9.11 (1H, br-t, J=6.0 Hz), 8.21 (1H, dd, J=8.4, 1.8 Hz), 7.72 (1H, s), 7.61 (1H, d, J=1.8 Hz), 7.57 (1H, dd, J=8.4, 1.8 Hz), 7.38-7.44 (1H, m), 7.26-7.23 (1H, m), 7.03-7.08 (1H, m), 6.96 (1H, d, J=8.4 Hz), 6.63 (1H, t, J=75.0 Hz), 4.69 (1H, sept., J=6.0 Hz), 4.59 (2H, d, J=6.0 Hz), 4.29 (2H, t, J=5.4 Hz), 3.89-3.94 (2H, m), 2.07-2.13 (2H, m), 1.41 (6H, d, J=6.0 Hz).

Synthesis of Compound (11n)

0.18 g of compound (ix) was dissolved in 2 ml of N,N-dimethylformamide, and 0.18 g of potassium carbonate and 0.12 ml of isopropyl bromide were added thereto, followed by stirring at room temperature for 16 hours and at 45° C. for 4 hours. Water was added thereto with ice cooling, and extraction was performed with ethyl acetate. The organic layer was washed with a saturated sodium chloride solution one time and concentrated under reduced pressure. The obtained residue was purified by silica gel column chromatography (n-hexane:ethyl acetate=2:1), thereby obtaining 0.16 g of methyl 2-(3-isopropoxy-4-difluoromethoxyphenyl)oxazole-4-carboxylate (methyl 2-(4-(difluoromethoxy)-3-isopropoxyphenyl)oxazole-4-carboxylate: compound (11n)) as a white powder.

$^1$H-NMR (CDCl$_3$) δ: 8.28 (1H, s), 7.74 (1H, d, J=1.8 Hz), 7.66 (1H, dd, J=8.4, 1.8 Hz), 7.25 (1H, d, J=8.4 Hz), 6.63 (1H, t, J=74.7 Hz), 4.71 (1H, sept., J=6.0 Hz), 3.96 (3H, s), 1.39 (6H, d, J=6.0 Hz).

Synthesis of Compound (11o)

0.7 g of compound (11n) was dissolved in 7 ml of methanol, and 1.4 ml of a 25% sodium hydroxide aqueous solution was added thereto, followed by heating under reflux at room temperature for 30 minutes. The reaction solution was stirred with ice cooling, and concentrated hydrochloric acid was added thereto to give a pH of 3, followed by collection of the precipitated crystals by filtration. The obtained crystals were dried under reduced pressure, thereby obtaining 2-(3-isopropoxy-4-difluoromethoxyphenyl)oxazole-4-carboxylic acid (2-(4-(difluoromethoxy)-3-isopropoxyphenyl)oxazole-4-carboxylic acid: compound (11o)).

¹H-NMR (CDCl₃) δ: 8.38 (1H, s), 7.74 (1H, d, J=1.8 Hz), 7.66 (1H, dd, J=8.1 Hz, 1.8 Hz), 7.25 (1H, d, J=8.1 Hz), 6.64 (1H, t, J=75 Hz), 4.72 (1H, sept, J=6.3 Hz), 1.40 (6H, d, J=6.3 Hz).

Synthesis of Compound (11p)

The procedure in "Synthesis of Compound (11i)" above was repeated using compound (iii) and 2-ethoxy-6-hydroxy benzoic acid, thereby obtaining N-[2-(3-isopropoxy-4-difluoromethoxyphenyl)oxazol-4-ylmethyl]-2-ethoxy-6-hydroxybenzamide (N-((2-(4-(difluoromethoxy)-3-isopropoxyphenyl)oxazol-4-yl)methyl)-2-ethoxy-6-hydroxybenzamide: compound (11p)).

¹H-NMR (CDCl₃) δ: 13.81 (1H, s), 9.00 (1H, brs), 7.68-7.62 (2H, m), 7.60 (1H, dd, J=8.4 Hz, 2.1 Hz), 7.30-7.18 (2H, m), 6.63 (1H, t, J=75 Hz), 6.61 (1H, d, J=8.4 Hz), 6.37 (1H, d, J=8.1 Hz), 4.69 (1H, sept, J=6.0 Hz), 4.60 (2H, dd, J=5.1 Hz, 0.9 Hz), 4.15 (2H, dd, J=14.1 Hz, 6.9 Hz), 1.48 (3H, t, J=6.9 Hz), 1.40 (6H, d, J=6.3 Hz).

Synthesis of Compound (11q)

The procedure in "Synthesis of Compound (11i)" above was repeated using compound (iii) and 2-ethoxy-3,4-dihydroxybenzoic acid, thereby obtaining N-[2-(3-isopropoxy-4-difluoromethoxyphenyl)oxazol-4-ylmethyl]-2-ethoxy-3,4-dihydroxybenzamide (N-((2-(4-(difluoromethoxy)-3-isopropoxyphenyl)oxazol-4-yl)methyl)-2-ethoxy-3,4-dihydroxybenzamide: compound (11q)).

¹H-NMR (d6-DMSO) δ: 9.83 (1H, brs), 8.65 (1H, brs), 8.54 (1H, t, J=5.4 Hz), 8.10 (1H, s), 7.63 (1H, d, J=1.8 Hz), 7.56 (1H, dd, J=8.4 Hz, 1.8 Hz), 7.33 (1H, d, J=8.4 Hz), 7.21 (1H, d, J=8.7 Hz), 7.15 (1H, t, J=74 Hz), 6.62 (1H, d, J=8.4 Hz), 4.73 (1H, sept, J=6.0 Hz), 4.45 (2H, d, J=5.4 Hz), 4.03 (2H, dd, J=14.1 Hz, 7.2 Hz), 1.32 (6H, d, J=6.0 Hz), 1.25 (3H, t, J=7.2 Hz).

Synthesis of Compound (11r)

A typical synthesis procedure was performed using 0.1 g of compound (11a) and chlorosulfuric acid, thereby obtaining N-[(2-(3-isopropoxy-4-difluoromethoxyphenyl)oxazol-4-yl)methylcarbamoyl]-2-phenyl ammonium sulfate (ammonium 2-((2-(4-(difluoromethoxy)-3-isopropoxyphenyl)oxazol-4-yl)methylcarbamoyl)phenyl sulfate (compound (11r)) as a white powder. The melting point was 162.0° C.

Synthesis of Compound (11s)

A typical synthesis procedure was performed using 0.1 g of compound (11a), 1-bromo-2,3,4-tri-O-acetyl-α-D-glucuronic acid methyl, and silver oxide, thereby obtaining (2S,3S,4S,5R,6S)-6-(2-((2-(3-isopropoxy-4-difluoromethoxyphenyl)oxazol-4-yl)methylcarbamoyl)phenyl)-3,4,5-trihydroxytetrahydro-2H-pyran-2-carboxylic acid ((2S,3S,4S,5R,6S)-6-(2-((2-(4-(difluoromethoxy)-3-isopropoxyphenyl)oxazol-4-yl)methylcarbamoyl)phenoxy)-3,4,5-trihydroxytetrahydro-2H-pyran-2-carboxylic acid: compound (11s)) as a white powder. The melting point was 163.6° C.

Production Example 7: Production of Formulations

Study of Solvent

To select a solvent for dissolving compound (11) in preparing an ointment containing compound (11), the solubility of compound (11) in various solvents was studied. Even a solvent having a high solubility of compound (11) exhibits reduced solubility of compound (11) if it has compatibility with a base material (ointment base), such as petrolatum or paraffin, and is mixed with the base material. Such a case may result in precipitation of compound (11). Thus, a solvent that has a high solubility of compound (11) but that has no or low miscibility (compatibility) with petrolatum or paraffin is relatively preferable for use. Table 4 shows the results of the study.

TABLE 4

| Solvent | Miscibility of Compound (11) Solvent Solution with Petrolatum | Solubility (W/W %) |
|---|---|---|
| Triacetine | Immiscible | 32.5 |
| Propylene carbonate | Immiscible | 56.9 |
| Diethyl sebacate | Miscible | 42.6 |
| Diisopropyl adipate | Miscible | 40.3 |
| Isostearic acid | Miscible | 19.8 |
| Olive oil | Miscible | 6.1 |
| Isopropyl myristate | Miscible | 6.0 |
| Hexyldodecanol | Miscible | 5.4 |
| Isostearyl alcohol | Miscible | 5.1 |
| Decyl oleate | Miscible | 2.6 |
| Liquid Paraffin | Miscible | 0.1 |

Table 4 indicates that triacetin and propylene carbonate have low miscibility with petrolatum, and also indicates that triacetin and propylene carbonate have a relatively high solubility of compound (11).

Formulation of Ointment

Ointments (Examples 1 to 10 and Comparative Examples 1 to 8) were prepared as described below. As noted above, solvents that dissolve compound (11) were found. Thus, the present invention encompasses all of the ointments prepared by dissolving compound (11) in a solvent. However, of these, the following describes particularly preferable examples as Examples, and others as Comparative Examples for convenience. The particle size of droplets is measured by placing a suitable amount of a prepared ointment on a glass slide and observing the droplet size with a polarizing microscope.

Example 1

73.0 g of white petrolatum, 10.0 g of liquid paraffin, 3.0 g of paraffin, and 1.0 g of beeswax (non-chemically bleached beeswax) were heated and dissolved at 70° C. in an agi-homomixer. Thereafter, a solution of 3.0 g of compound (11) in 10.0 g of propylene carbonate was further added thereto, and the mixture was stirred with a homomixer at 5000 rpm and with a paddle at 30 rpm. The homomixer was then turned off at 45° C., and the paddle and cooling were turned off at 40° C. to give a droplet size of 20 μm or less. Thereafter, the resulting product was inserted into aluminum tubes, 5 g in each tube, with a YS-7 filling machine, and the tubes were sealed, thereby obtaining ointments.

Example 2

The procedure of Example 1 was repeated except that 72.0 g of white petrolatum and 2.0 g of beeswax were used, thereby obtaining ointments.

Example 3

The procedure of Example 1 was repeated except that 70.5 g of white petrolatum and 3.5 g of beeswax were used, thereby obtaining ointments.

Example 4

The procedure of Example 1 was repeated except that 81.0 g of white petrolatum, 1.0 g of compound (11), and 4.0 g of propylene carbonate were used, thereby obtaining ointments.

Example 5

The procedure of Example 4 was repeated except that 80.0 g of white petrolatum and 2.0 g of beeswax were used, thereby obtaining ointments.

Example 6

The procedure of Example 4 was repeated except that 78.5 g of white petrolatum and 3.5 g of beeswax were used, thereby obtaining ointments.

Example 7

The procedure of Example 6 was repeated except that 79.2 g of white petrolatum and 0.3 g of compound (11) were used, thereby obtaining ointments.

Example 8

The procedure of Example 6 was repeated except that 79.4 g of white petrolatum and 0.1 g of compound (11) were used, thereby obtaining ointments.

Example 9

70.5 g of white petrolatum, 10.0 g of liquid paraffin, 3.0 g of paraffin, and 3.5 g of beeswax (chemically bleached beeswax) were heated and dissolved at 70° C. in an agi-homomixer. Thereafter, a solution of 3.0 g of compound (11) in 10.0 g of propylene carbonate was further added thereto, and the mixture was stirred with a homomixer at 5000 rpm and with a paddle at 30 rpm. The homomixer was then turned off at 45° C., and the paddle and cooling were turned off at 40° C. to give a droplet size of 20 μm or less. Thereafter, resulting product was inserted into aluminum tubes, 5 g in each tube, with a YS-7 filling machine, and the tubes were sealed, thereby obtaining ointments.

Example 10

The procedure of Example 3 was repeated except that 73.5 g of white petrolatum and 7.0 g of propylene carbonate were used, thereby obtaining ointments.

Comparative Example 1

The procedure of Example 4 was repeated except that 82.0 g of white petrolatum was used, and that beeswax was not added, thereby obtaining ointments.

Comparative Example 2

58.5 g of white petrolatum, 6.0 g of paraffin, 6.0 g of beeswax, and 5.0 g of diethyl sebacate were heated and dissolved at 70° C. by hand stirring in a 200-mL beaker. After cooling to 50° C., 17 g of liquid paraffin was added thereto, and the mixture was heated to 50° C. 13 g of a paste containing 10 g of liquid paraffin and 3 g of micronized compound (11) was added thereto and mixed well by hand stirring, with the temperature maintained at 50° C. The mixture was cooled to room temperature with ice water. Thereafter, the mixture was inserted into aluminum tubes, 5 g in each tube, with a YS-7 filling machine, thereby obtaining ointments.

Micronized compound (11) was obtained by adding compound (11) to liquid paraffin and pulverizing the mixture with a DYNO-MILL (bead mill). Thus-obtained paste was used in the operation above.

Comparative Example 3

The procedure of Example 3 was repeated except that 75.5 g of white petrolatum and 5.0 g of propylene carbonate were used, thereby obtaining ointments.

Comparative Example 4

The procedure of Example 6 was repeated except that 80.5 g of white petrolatum and 2.0 g of propylene carbonate were used, thereby obtaining ointments.

Comparative Example 5

The procedure of Example 6 was repeated except that 79.5 g of white petrolatum was used, and that compound (11) was not added, thereby obtaining ointments.

Comparative Example 6

The procedure of Example 3 was repeated except that the mixture was stirred with a homomixer at 1500 rpm and with a paddle at 15 rpm, thereby preparing an ointment having a droplet size of about 50 μm.

Comparative Example 7

The procedure of Example 6 was repeated except that the mixture was stirred with a homomixer at 1500 rpm and with a paddle at 15 rpm, thereby preparing an ointment having a droplet size of about 50 μm.

Comparative Example 8

The procedure of Example 7 was repeated except that the mixture was stirred with a homomixer at 1500 rpm and with a paddle at 15 rpm, thereby preparing an ointment having a droplet size of about 50 μm.

Table 5 shows the compositions of formulations described above.

TABLE 5

| Formulation | Component and Amount of Component (w/w %) | | | | | | | State of Formulation | droplet Size (Particle Size) |
|---|---|---|---|---|---|---|---|---|---|
| | Compound(11) | White Petrolatum | Liquid Paraffin | Paraffin | Beeswax | Propylene Carbonate | Diethyl Sebacate | | |
| Example 1 | 3 | 73 | 10 | 3 | 1 | 10 | — | Homogeneous droplet-dispersion ointment | 20 μm or less |

TABLE 5-continued

| Formulation | Compound(11) | White Petrolatum | Liquid Paraffin | Paraffin | Beeswax | Propylene Carbonate | Diethyl Sebacate | State of Formulation | droplet Size (Particle Size) |
|---|---|---|---|---|---|---|---|---|---|
| Example 2 | 3 | 72 | 10 | 3 | 2 | 10 | — | Homogeneous droplet-dispersion ointment | 20 μm or less |
| Example 3 | 3 | 70.5 | 10 | 3 | 3.5 | 10 | — | Homogeneous droplet-dispersion ointment | 20 μm or less |
| Example 4 | 1 | 81 | 10 | 3 | 1 | 4 | — | Homogeneous droplet-dispersion ointment | 20 μm or less |
| Example 5 | 1 | 80 | 10 | 3 | 2 | 4 | — | Homogeneous droplet-dispersion ointment | 20 μm or less |
| Example 6 | 1 | 78.5 | 10 | 3 | 3.5 | 4 | — | Homogeneous droplet-dispersion ointment | 20 μm or less |
| Example 7 | 0.3 | 79.2 | 10 | 3 | 3.5 | 4 | — | Homogeneous droplet-dispersion ointment | 20 μm or less |
| Example 8 | 0.1 | 79.4 | 10 | 3 | 3.5 | 4 | — | Homogeneous droplet-dispersion ointment | 20 μm or less |
| Example 9 | 3 | 70.5 | 10 | 3 | 3.5 | 10 | — | Homogeneous droplet-dispersion ointment | 20 μm or less |
| Example 10 | 3 | 73.5 | 10 | 3 | 3.5 | 7 | — | Homogeneous droplet-dispersion ointment | 20 μm or less |
| Comparative Example 1 | 1 | 82 | 10 | 3 | — | 4 | — | Homogeneous droplet-dispersion ointment | 20 μm or less |
| Comparative Example 2 | 3 | 58.5 | 27 | 6 | 5 | — | 5 | Homogeneous ointment in which crystals are dispersed | 20 μm or less (crystalline particle size) |
| Comparative Example 3 | 3 | 75.5 | 10 | 3 | 3.5 | 5 | — | Homogeneous ointment | — |
| Comparative Example 4 | 1 | 80.5 | 10 | 3 | 3.5 | 2 | — | Homogeneous ointment | — |
| Comparative Example 5 | — | 79.5 | 10 | 3 | 3.5 | 4 | — | Homogeneous droplet-dispersion ointment | — |
| Comparative Example 6 | 3 | 70.5 | 10 | 3 | 3.5 | 10 | — | Inhomogeneous droplet-dispersion ointment | More than 50 μm |
| Comparative Example 7 | 1 | 78.5 | 10 | 3 | 3.5 | 4 | — | Inhomogeneous droplet-dispersion ointment | More than 50 μm |
| Comparative Example 8 | 0.3 | 79.2 | 10 | 3 | 3.5 | 4 | — | Inhomogeneous droplet-dispersion ointment | More than 50 μm |

Study into Formulation Stability 1

The ointments prepared in Comparative Example 1 and Examples 4, 5, and 6 were allowed to stand at 40° C. for 2 months. Thereafter, the dispersion state of the propylene carbonate solution in each formulation was examined. Table 6 shows the results. Table 6 reveals that beeswax maintains the homogeneous dispersion state, and thus improves stability.

TABLE 6

| Formulation | Amount of Beeswax | Dispersion State |
|---|---|---|
| Comparative Example 1 | 0 | The particle size was increased. |
| Example 4 | 1.0 | Excellent |
| Example 5 | 2.0 | Excellent |
| Example 6 | 3.5 | Excellent |

Study into Formulation Stability 2

The ointments prepared in Comparative Example 1 and Examples 1 to 6 are different in the amount of beeswax added. These formulations were subjected to a stability test at 50° C. for 2 weeks, 4 weeks, or 6 weeks. To examine the degree of decomposition of compound (11), the amount of generated 3-(2-propoxy 3-difluoromethoxy)benzamide, which is one of the decomposed matters, was measured by high-performance liquid chromatography. Table 7 shows the results. The values in Table 7 indicate the concentration (wt %) of compound (11), beeswax, and the decomposed matter in each formulation. While Comparative Example 1, to which beeswax was not added, generated about 1% of the decomposed matter, the formulations made by adding beeswax exhibited reduced generation of the decomposed matter.

TABLE 7

| Formulation | Concentration of Compound (11) (%) | Amount of Beeswax Added (%) | After 2 weeks | After 4 weeks | After 6 weeks |
|---|---|---|---|---|---|
| Comparative Example 1 | 1.0 | 0 | 0.90 | 0.99 | 0.97 |
| Example 4 | 1.0 | 1.0 | 0.00 | <0.05 | <0.05 |
| Example 5 | 1.0 | 2.0 | 0.00 | 0.00 | 0.00 |
| Example 6 | 1.0 | 3.5 | 0.00 | <0.05 | <0.05 |
| Example 1 | 3.0 | 1.0 | <0.05 | 0.23 | 0.18 |
| Example 2 | 3.0 | 2.0 | 0.00 | 0.00 | <0.05 |
| Example 3 | 3.0 | 3.5 | 0.00 | 0.00 | <0.05 |

Study into Formulation Stability 3

The formulation of the formulation of Example 3 was prepared using beeswax that was not bleached (unbleached beeswax), beeswax bleached by non-chemical purification (non-chemically bleached beeswax), or beeswax that was chemically bleached (chemically bleached beeswax) as beeswax, and the formulation was inserted into aluminum tubes, and sealed, followed by storage at 50° C. for 2 weeks, 4 weeks, or 8 weeks. In the same manner as above, with the generated decomposed matter of compound (11) (3-(2-propoxy 3-difluoromethoxy)benzamide) as an index, the stability of compound (11) was examined. Table 8 shows the results. While the use of chemically bleached beeswax generated a high amount of the decomposed matter, the use of non-chemically bleached beeswax and unbleached beeswax exhibited reduced generation of the decomposed matter.

TABLE 8

| Type of Beeswax | After 2 Weeks | After 4 weeks | After 8 weeks |
|---|---|---|---|
| Chemically Bleached Beeswax Produced by Company A | 0.19 | 0.20 | 0.16 |
| Non-Chemically Bleached Beeswax Produced by Company A | 0.00 | 0.00 | 0.00 |
| Unbleached Beeswax Produced by Company A | 0.00 | 0.00 | 0.00 |
| Non-Chemically Bleached Beeswax Produced by Company C | 0.00 | 0.00 | 0.00 |
| Chemically Bleached Beeswax Produced by Company D | 0.18 | 0.16 | 0.25 |

Study into Formulation Stability 4

Ointments containing compound (11) and different amounts of beeswax were prepared. A predetermined amount of each ointment was placed on a glass slide, and the droplet size of each ointment was confirmed with a polarizing microscope to search for the amount of beeswax necessary to obtain an ointment in which droplets are excellently dispersed. The ointments (Examples 11 to 19 and Comparative Examples 9 to 11) were prepared as described below. The present invention encompasses all of the ointments containing beeswax. However, of these, the following describes particularly preferable examples as Examples, and others as Comparative Examples for convenience.

Example 11

141.0 g of white petrolatum, 20.0 g of liquid paraffin, 6.0 g of paraffin, and 7.0 g of beeswax (non-chemically bleached beeswax) were heated and dissolved at 70° C. in an agi-homomixer. Thereafter, a solution of 6.0 g of compound (11) in 20.0 g of propylene carbonate was further added thereto, and the mixture was stirred with a homomixer at 5000 rpm and with a paddle at 30 rpm, followed by cooling. The homomixer was turned off at 45° C. and the paddle and cooling were turned off at 40° C. The resulting product was inserted into aluminum tubes, 5 g in each tube, with a YS-7 filling machine, and the tubes were sealed, thereby obtaining ointments.

Example 12

The procedure of Example 11 was repeated except that 146.0 g of white petrolatum and 2.0 g of beeswax were used, thereby obtaining ointments.

Example 13

The procedure of Example 11 was repeated except that 146.4 g of white petrolatum and 1.6 g of beeswax were used, thereby obtaining ointments.

Example 14

The procedure of Example 11 was repeated except that 146.8 g of white petrolatum and 1.2 g of beeswax were used, thereby obtaining ointments.

Comparative Example 9

The procedure of Example 11 was repeated except that 147.2 g of white petrolatum and 0.8 g of beeswax were used, thereby obtaining ointments.

Comparative Example 10

The procedure of Example 11 was repeated except that 147.6 g of white petrolatum and 0.4 g of beeswax were used, thereby obtaining ointments.

Example 15

157.0 g of white petrolatum, 20.0 g of liquid paraffin, 6.0 g of paraffin, and 7.0 g of beeswax (non-chemically bleached beeswax) were heated and dissolved at 70° C. in an agi-homomixer. Thereafter, a solution of 2.0 g of compound (11) in 8.0 g of propylene carbonate was further added thereto, and the mixture was stirred with a homomixer at 5000 rpm and with a paddle at 30 rpm, followed by cooling. The homomixer was turned off at 45° C., and the paddle and cooling were turned off at 40° C. The resulting product was inserted into aluminum tubes, 5 g in each tube, with a YS-7 filling machine, and the tubes were sealed, thereby obtaining ointments.

Example 16

The procedure of Example 15 was repeated except that 162.0 g of white petrolatum and 2.0 g of beeswax were used, thereby obtaining ointments.

Example 17

The procedure of Example 15 was repeated except that 162.4 g of white petrolatum and 1.6 g of beeswax were used, thereby obtaining ointments.

Example 18

The procedure of Example 15 was repeated except that 162.8 g of white petrolatum and 1.2 g of beeswax were used, thereby obtaining ointments.

Example 19

The procedure of Example 15 was repeated except that 163.2 g of white petrolatum and 0.8 g of beeswax were used, thereby obtaining ointments.

Comparative Example 11

The procedure of Example 15 was repeated except that 163.6 g of white petrolatum and 0.4 g of beeswax were used, thereby obtaining ointments.

Table 9 shows the formulations and the state of the dispersion of droplets of the ointments. The unit is wt %. Table 9 reveals that when an ointment containing 3 parts by weight of component (11) contains 0.6 parts by weight or more of beeswax, the ointment exhibits particularly excellent dispersion of the droplets, and that when an ointment containing 1 part by weight of compound (11) contains 0.4 parts by weight or more of beeswax, the ointment exhibits particularly excellent dispersion of the droplets.

TABLE 9

| Formulation | Compound(11) | White Petrolatum | Liquid Paraffin | Paraffin | Beeswax | Propylene Carbonate | State of Formulation |
|---|---|---|---|---|---|---|---|
| Example 11 | 3.0 | 70.5 | 10.0 | 3.0 | 3.5 | 10.0 | Droplet-dispersion ointment having a particle size of 20 µm or less |
| Example 12 | 3.0 | 73.0 | 10.0 | 3.0 | 1.0 | 10.0 | Droplet-dispersion ointment having a particle size of 20 µm or less |
| Example 13 | 3.0 | 73.2 | 10.0 | 3.0 | 0.8 | 10.0 | Droplet-dispersion ointment having a particle size of 20 µm or less |
| Example 14 | 3.0 | 73.4 | 10.0 | 3.0 | 0.6 | 10.0 | Droplet-dispersion ointment having a particle size of 20 µm or less |
| Comparative Example 9 | 3.0 | 73.6 | 10.0 | 3.0 | 0.4 | 10.0 | Droplet-dispersion ointment having a particle size of 20 µm or less |
| Comparative Example 10 | 3.0 | 73.8 | 10.0 | 3.0 | 0.2 | 10.0 | Droplet-dispersion ointment having a particle size of more than 50 µm |
| Example 15 | 1.0 | 78.5 | 10.0 | 3.0 | 3.5 | 4.0 | Droplet-dispersion ointment having a particle size of 20 µm or less |
| Example 16 | 1.0 | 81.0 | 10.0 | 3.0 | 1.0 | 4.0 | Droplet-dispersion ointment having a particle size of 20 µm or less |
| Example 17 | 1.0 | 81.2 | 10.0 | 3.0 | 0.8 | 4.0 | Droplet-dispersion ointment having a particle size of 20 µm or less |
| Example 18 | 1.0 | 81.4 | 10.0 | 3.0 | 0.6 | 4.0 | Droplet-dispersion ointment having a particle size of 20 µm or less |
| Example 19 | 1.0 | 81.6 | 10.0 | 3.0 | 0.4 | 4.0 | Droplet-dispersion ointment having a particle size of 20 µm or less |
| Comparative Example 11 | 1.0 | 81.8 | 10.0 | 3.0 | 0.2 | 4.0 | Droplet-dispersion ointment having a particle size of more than 20 µm |

The invention claimed is:

1. An ointment comprising an oxazole compound represented by the following formula (11):

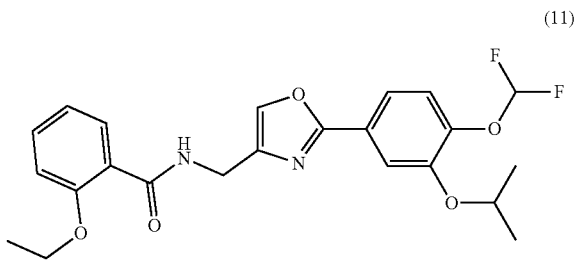 [SMILES: CCOc1ccccc1C(=O)NCc1coc(-c2ccc(OC(F)F)c(OC(C)C)c2)n1]

(11)

and a base component,
wherein the base component comprises a solvent for dissolving the oxazole compound in the solvent and an ointment base for dispersing or dissolving the solvent in the ointment base,
the oxazole compound is dissolved in the solvent for dissolving the oxazole compound, and
the solvent for dissolving the oxazole compound is at least one member selected from the group consisting of ethylene carbonate, propylene carbonate, benzyl alcohol, and triacetin.

2. The ointment according to claim 1, wherein the solvent for dissolving the oxazole compound is selected from the group consisting of (i) only ethylene carbonate, (ii) only propylene carbonate, (iii) ethylene carbonate with benzyl alcohol and/or triacetin, or (iv) propylene carbonate with benzyl alcohol and/or triacetin.

3. The ointment according to claim 1, wherein the base component comprises more than 2 parts by weight and 30 parts by weight or less of the solvent for dissolving the oxazole compound in the solvent, per part by weight of the oxazole compound, and 5 to 5000 parts by weight of the ointment base for dispersing or dissolving the solvent in the ointment base, per part by weight of the oxazole compound.

4. The ointment according to claim 1, wherein the ointment base comprises a hydrocarbon.

5. The ointment according to claim 1, wherein the ointment base is an ointment base for dispersing the solvent in the ointment base, and the solvent in the form of droplets, in which the oxazole compound is dissolved, is dispersed in the ointment base.

6. The ointment according to claim 1, wherein the ointment base comprises at least beeswax.

7. The ointment according to claim 6, wherein the beeswax is not chemically bleached.

8. The ointment according to claim 5, wherein the droplets have a mean particle size of 100 μm or less.

* * * * *